US007671187B2

(12) United States Patent
Aguirre et al.

(10) Patent No.: US 7,671,187 B2

(45) Date of Patent: Mar. 2, 2010

(54) IDENTIFICATION OF THE GENE AND MUTATION RESPONSIBLE FOR PROGRESSIVE ROD-CONE DEGENERATION IN DOG AND A METHOD FOR TESTING SAME

(75) Inventors: Gustavo Aguirre, Philadelphia, PA (US); Gregory M. Acland, Kennett Square, PA (US); Barbara Zangerl, Philadelphia, PA (US); Orly Goldstein, Ithaca, NY (US); Susan Pearce-Kelling, Berkshire, NY (US); Jeanette S. Felix, Horseheads, NY (US); Duska J. Sidjanin, Brookfield, WI (US)

(73) Assignee: Cornell Research Foundation, Inc., Ithaca, NY (US)

( * ) Notice: Subject to any disclaimer, the term of this patent is extended or adjusted under 35 U.S.C. 154(b) by 276 days.

(21) Appl. No.: 11/983,870

(22) Filed: Nov. 13, 2007

(65) Prior Publication Data

US 2009/0111976 A1 Apr. 30, 2009

Related U.S. Application Data

(62) Division of application No. 11/157,743, filed on Jun. 21, 2005, now Pat. No. 7,312,037.

(60) Provisional application No. 60/581,499, filed on Jun. 21, 2004.

(51) Int. Cl.
*C07H 21/04* (2006.01)
*C12Q 1/68* (2006.01)

(52) U.S. Cl. .................................... 536/23.1; 536/24.3

(58) Field of Classification Search ....................... None
See application file for complete search history.

(56) References Cited

U.S. PATENT DOCUMENTS 5,804,388 A 9/1998 Aguirre et al.

FOREIGN PATENT DOCUMENTS

WO 9902731 A1 1/1999
WO 0029615 A2 5/2000

OTHER PUBLICATIONS

Acland et al.; A Novel Retinal Degeneration Locus Identified by Linkage and Comparative Mapping of Canine Early Retinal Degeneration; Genomics, 1999, vol. 59; pp. 134-142.

Caase et al.; A Gene Potentially Involved in Progressive Rod—Cone Degeneration (PRCD); Annual Meeting of the Association for Research in Vision and Ophthalmology, May 2003, Abstract No. 2318, vol. 2003; Biosis Online Biosciences Information Service; 2 pages.

Sargan et al.; Use of Flow-Sorted Canine Chromosomes in the Assignment of Canine Linkage, Radiation Hybrid, and Syntenic Groups to Chromosomes: Refinement and Verification of the Comparative Chromosome Map for Dog and Human; Genomics, Oct. 15, 2000, vol. 69, No. 2; pp. 182-195.

Sidjanin et al.; Radiation hybrid map, physical map, and low-pass genomic sequence of the canine prcd region on CFA9 and comparative mapping with the syntenic region on human chromosome 17; Genomics, 2003, vol. 81; pp. 138-148.

*Primary Examiner*—Jeanine A Goldberg
(74) *Attorney, Agent, or Firm*—Hodgson Russ LLP

(57) ABSTRACT

Tools and methods are provided for determining whether or not a dog is genetically normal, is a carrier of, or is affected with or predisposed to progressive rod-cone degeneration. The method is based on the detection of a transversion from G to A at position corresponding to nucleotide position 1298 of SEQ ID NO: 1.

2 Claims, 11 Drawing Sheets

```
   1 CGGCCAGGTG GCACCTCTGA CTCCCAGCCC AAACCTGATG CCAGTGTCCA
  51 CTTCTCCCTG TCGCTCCCTC GCGACCCCGC CCTTCTCAAG ACTTGGTGTC
 101 CCTCTGCAAG TGTGAGAAGA GGTCGGCTCA CCTCTTCCGC TTTGGCTTAT
 151 GTATTTTAAA AATCGTTTTT CAAAGTAGAG AGCCCAGGTG CAGCCCCAGC
 201 TCTGGCCCTC CCTGGGAGCC TGGGCAGGAG ACCCCTTGAC ACCGCTTCCA
 251 TCTCCTTGGA GGGAAGGAAA ATCTAGTGCA GACCYCTGGG GTTTTTGGAG
 301 AGGGCTGGAG GAAGCTGGAT GCTCAGACCC CTGTGTGCTC CACATGCTGC
 351 CTGGGCCACC TCACTGAACC CCTCTGACAG GACACCCGAT GCCTGTGCGG
 401 TGCCCTTCCA AGTGGCTGCT CAGAAGCTTT GCACTGGGAA AGCAAGTATT
 451 CGCTATTTCT ATTTAGTATT TCTATTTAGC TTTATCTCAT CTTTTACAAG
 501 TCTTATGTGT GTTTATTATG CAGGACTGTA TTCGCACAGA TGTGGAAGAT
 551 CTAATGTATG AGCAGATGCA TATACTTATT TCATGAGTGC ACACTTAAAT
 601 CCAGTCTTTT ATGGAAGGGG CTATGGAAAT CAGTAACATT TGGGGAGGAC
 651 TGTCCAGAGG GGAGAACACA ACTGCTCAGC CGCCCCTCCA CTCCCCGGCC
 701 TCCCTTGTCT TTCTGGCTTC ATTATCTAAT ATTCTTCCTC CCCTCCCCAT
 751 GGCTCTCCAT GACATCATTG TTCTGCCAAC ACTCAACTTC CAGTTGCTGG
 801 AACATGCTCT GTGCTTTTGT GTCAGCCGCC CCGGAAGAGT CTTCTGTTGG
 851 SGGGGAGGTA ACCTTCCTTG AACACCTGCA AATTCCAATG CCCCCAGCTC
 901 CTCTCCCAAG CATTCCCTGA CACATGCAAC TCCGAAAGTG CTCTGCGGGT
 951 GCCTCTCATC ACCCAAGTCG CTCTACTGTG GTCATTAATG TGACTTGCYA
1001 GCTCAAGTGT CTAGACTAGA AGCCCCTTGA GGGTTAGGCC CAGGTCCTAG
1051 TCACATCTGT ATCCAGAATG GACAGCTTGA TTTACCCTGC CACCGCAGGC
1101 GACAACTTGG GCCCAGTGAG GTTAATCAGT CTGCACAAGG TCGGGTTGGC
1151 TGACCCCACT AATCAGCTTG AGCCTCCTAA TCCAGTGGCA GCAGGAACCT
1201 CAGGATGGGC AGCAGTGGCT TGTGAGAGCC GGCAGGGCCA TTTTGGCCTT
1251 TCTCCTGCAG ACTCTGTCCG GGAGGGGATG GGGCAGCTGA GCCATGTRCA
1301 CCACCCTCTT CCTACTCAGC ACCTTGGCCA TGCTCTGGCG CCGCCGGTTC
1351 GCCAACCGGG TCCAACCgtg agaagctgat ggggccatgg gcagggatgg
1401 ggagagagga gaagctaggg ggtgaggggt ggtgcagggg ctgcctggac
1451 ctcctgggag gctggagggc ggggaggatt tgcagggagg tccagagagg
1501 tttcccatca gagcacgcgg gggcgggggc tcgcaggtgc tccgagactg
1551 gctggagtcc ccggtccccc agcccaacac ggccaggaga gggggttctg
1601 ggcccgggcg ctgcccacag ctcttccagc ctcttcctcc cgcccacagG
1651 GAGCCCAGCG GAGCAGACGG GGCAGTCGTG GGCAGCAGGT CGGAGAGAGA
1701 CCTCCAGTCC TCGGGCAGgt aaggcagagt ctgggctggg ggaggcaggg
1751 tgcgtcgagg aagcggctgc cctggccgcc ccgaccgtgc ctgggcaggt
1801 acatgagtgc acccgagccg gcgcgccggg gcccctcgcc ccagccaccc
1851 ggtccccgtg tgcccggtgg gcagcctcgg tgtctgtgct cccccgcggc
1901 actgggcgcc csggcctgtc ctctgcaccg cagctgctct gctttgcccg
1951 agtgcggggt ggtcccccgg gtcccatcgg aaggcgcggg gggaccggag
2001 aggatggggc aggagcagct ccgggcggcc ggctcgctgc ccttcccccct
2051 ccccgcggcc cccgctccgc ctcagccgct cccctgcccc ggccgccggc
2101 gggattcgcc caccggcccc caataggagg cgcaggagcg gcatgacgtc
2151 atcggcaccg cctgccattg gctgggcagc tcctgcgggc aggtcgctgt
2201 ctccagcggc cgaaagttaa ctcttcccta ggccgaagcc atgtggctcc
2251 acaagggggg aagtttgggg aacttctgga ttcttccttc cctgggtgac
2301 cagtgtcctt tgatgttagg ggctcctatg cccaacaaac cacggaaaaa
```

Figure 1A 2351 tcaacatgca tttattaaga acataccgtt gtgcgtgttc ttttgtgccc
2401 ccggacccac ctrgtgggg agtcctgtgt gaagggacat tctctcctgc
2451 aaaaggtcta ctagccttct ctcaactcta gtgagacaaa gcacatgatg
2501 cccttgggct ccggggcctg tggctggagg gagtctcccc acagcgctca
2551 gatggctgag ccagtgagcg tgcctgcctg ctggggcacy ccaccggctc
2601 tcctccrggt gtgtaggacc tgcctgggtg cccctcagcc atgtggagac
2651 tggcgagcca tgagaaatga gaatgggaat ctgtctccgt atgcggcccc
2701 aaattcctcy tcggtgctgg gattcctcca agctctgaat rtcaggaggg
2751 cagccctggg catgtgccyg agacaggtat ttctgggcca cccttccttg
2801 acaatctagg ctagctgaga tggtcatgat actacccaag taggcctgct
2851 ggtgaaatgg gctgacaaag gtgaaatgat gagcactggg cctcacgcag
2901 agcaggccct tgaatgacta gtcctccctg ttgagtttgg gtctggaggc
2951 ggacagccag agtccacatc ctgactccct gcttcctgac cgagagcctc
3001 tgggaaagct atgtgatctt tctatttgta tataaactgg gattaataac
3051 agaatggtgt gggggtgttt gtgaggttca aattgagatc atcctaaagc
3101 acttggcacg aaacagctrt ttaataaatg ccggctagct attctcctgt
3151 tgttacctgg ctcttgatca gtgttctatt cttcccttga ggtctcttaa
3201 acgttaactc acttggaagt tgtaacagcc ccagagggtt ggcaagacaa
3251 gtgtttctat ctcttgttaa tggtggagga aactgaggga aggggaggcg
3301 tcagtttttc actcgaggtc atccatccta tttgtggctg atggcaactg
3351 acttcaggta gtcggtctcc tctacatgaa atgggcctgg accctccctg
3401 tcaggagaaa aaagctgaat ctggaccatc tggcccagcc tcgtggggtc
3451 tagccagaag gaagcagttg cctgttaact cccagggacc cagttaactg
3501 gaaaaatcag cctaacatcc aacacctcct gcttcgggtg gctgttgtga
3551 agggctggtc tggggagcag taggcatgac atttctgctc tgcaattcca
3601 cagtcacaaa ttccagctga tttcctggct gctcctaccc ctcagtagtg
3651 gggtgcctcc ctaggcgtgg ggcaaaggga agaagtctgg aaagacggga
3701 aggacgtccc cttcaatcct ctgactccca tgcttttctg tttagAAAGG
3751 AAGAGCCTCT GAAGTAAGTC TTCACCCGGT CAGGCGGAGC TCGGCCCCAG
3801 GGAYTGGGAT CAGCTGGCAG AGGCAGgtag ggcagggctg caagccttgg
3851 aaggtagagg gctgggctgg ggacaaggca ggctctgcaa ggcctggcca
3901 tgagggagca gagctccatg gagggtacac agaaggcggg tggcctctca
3951 tcagctcctg cctcaagcct sctgtggtcc aggccatggc gcaaggcttt
4001 gttagtttta agggaagggc gtgtggtgaa gtggtggtca tgctggcact
4051 gtagtgccag aggacttcta agggagaggg tgtgctctgg aatatccatt
4101 ctgcaatgca agcccctgcc ttgggatggg aggaagtgcc aatctggttt
4151 tctatttcag TTCAAGTCCC GGCTGGCCTC TTACCCACAA AGCATGCTGT
4201 GGTGGAAGCA GCAGCAGCAG CAAGAAGAAA AATGGGAAAA AGCAGTCATC
4251 AAGAAGGTAG ACTCCTCCCT TTGAGTCCCT GGACCTGCCT GGCCTCCCTT
4301 TGCCCCAGAC CCTGGTGGTG GGGCTCCTGA AGCAAGGCCT GGCTGGGGCA
4351 GGCTGGAGGG CAAAGACGCT CATTGCCCTG GCTTGGGCTC CCTTCCTCTG
4401 AGATCCTGAG GATAGTCTGA GGCAGGCCCA GAGAGGGACT CAGGTTTCTT
4451 ATGGAAGGRC TTCTCATTCA TCCCTAATAT AATCCTTGCA ATGACCCAAG
4501 AAGACTGGGC GTGTTATTAT CCACACTTTT GGAAATGAGG AAACAGAGAG
4551 AGGTTAAGGA ATCTGTCCAG TGTCATCCAG CTAGTTAATC CTGCCCCCCA
4601 CCCCCACCCA CCCCCCGCCC TCCCAGCCTC CTTTGGAGGC TGCAGAGCCC

Figure 1B

```
4651  ACACTCTTAC CCACCAGGGC ACAGGCCTCT CTGAAATCAC CTGGAAGTTT
4701  GCAGCTTGCA GCTGCTATGT GAGAGCAGGG GTTCCACGGG CCCGGCAGCC
4751  CCAAAGCCTG TGGTCCAAGG CTGTGTGGTA TCAGTTTGCC ATGGTGGCGC
4801  TCTAGTTTCC AGGGCACTTG CCTCTCCCCG GTCCCCAGAG CTCACCCCGT
4851  CACCAGCCAC TCTGCTGCAG TTCTCAATAA GAAATGCCAG CTGGGATCTG
4901  TGACATGTCT GCCTGCGGCT GGAAGGAAGC ATCTCTCAAC CTGTCCTCTG
4951  AGCGTGTCTG CGTGCCTGTG TGCATGCGTG CGTGTGTTCC AAAGGGGCAG
5001  TCGCATGTGG GAAGGGAAGA AGCCTGACAC TTGTTCTTGT CAATCTGCTG
5051  ACTGCTCAGT ACCACGGCGG CTCTGCCATT TCTCCCTCAC AGTCCTGCTC
5101  GACCCAGAGC AGAGATCAAA GCAGATTTCC GCTTCTGCTC CCTGAGATCC
5151  AGGCGCAGAC CTGCAGGCAG CTGCTCCCCA CTGTCTGGAA GCCATTCATC
5201  ATGCAAAGCG CCTCCCCACC AAACCCCTGC CTGCACGTGC ATCRTCCCCC
5251  CACCATCACC ATCCAGCCCC CAGGGTGGGC AGGGAGGTCC CTGCCTAGCT
5301  GCACACCCCC CAGGCCATCA AGAGGCAGGA GATGGGGAGT TCTCTCGACA
5351  GCAGCCTGTC TGCCGCCCTG ACTCCACATC TGAGGGAAGG AAGGAAAGGG
5401  TGAGATGCCA CAGACAGAGG GGACCACGCT GAAGCCATGG GGGAGGGGCT
5451  GCTGATCTTG CCCTGGAAGC CTCTAGAAGT AGGGCAGGGT GGAGGCAGGG
5501  GAAGGGTCAA ACCAGGGGAA GGAGCTGTGC GCTGGAATGG CGACAGAGCC
5551  CCACCGCCCA CTCGACATGG GCCAGGAGTT CGTGACCACC TGTCTCAGCT
5601  CCTGTCAGCC TGTCTTTCTC CTGCGAGGTG TTGGCCTTCC TTGGTGACAG
5651  GGCTGTCGGG CTGAGGGCCA GGGGCACCGT TCCTGGGGCC CCCATCTKCG
5701  TCCCCGAGCC CACCTGTGTA TTCATCCTCT AATCTGTTTG CCATGCTCCT
5751  GTCACTTCAG CCTCGGCTCT GCTCTCTACC ATTTCCACGT TGCCTGCCTC
5801  CTTGCACTAG TCTGAGGAAT TGTCAGGCCA AGGTCACCTG GCTGGACAGG
5851  GGCTGGCCCA CGGCCCAGAC ACACCTCCAC GAGGCGACAC CCCTTCGCTG
5901  CACTGTTCTA GGGACCTGCT CAGGAGAGGG TGGCTCCTCT GGGCCTCGGT
5951  CCCAGAGGGA AGGAGAGAAG GGGAAGGGAA GGGCTGCTGG CGATGGGGGG
6001  ACTGTGTCGG CTGGCCTTGG CGGTTGCCCG GGCCCTGGCA GCTGGGGTGC
6051  CATGTGGGCT GGGCGGGAGG GGCCCTCTCC CCCAGGGAGC AGGCTGGCTT
6101  CGGTGGGAGC AGATTGTGTT TACACCTTCC CCACACACCC AGCCCACGCT
6151  CGCCTCTTAT TCCCCGGGAC TCTCCCACCC CTGGGCTCTC TCTGCACCAC
6201  GGGCACGTTT GCAGCTCCTC TCCTGCTGCA GGAAGTTGCC GCCCTCAGCA
6251  GAGMGCTCCT CTACAGAAGG CTGCCAGGGC CCAGGCGCTC CCTCCTCGGC
6301  CCACTATCTC CCGTCGTGGG GGGGGACCCA GTGTCCCCAA GAGGCTGAAT
6351  CCACCCACCC CCCATTTCCT TGGAAAACAG CTGCTGCTTG GGAATGGGGG
6401  CAGGAAGGAA AGCCCGGGGG GCTTGGCAGA CTTGACCATA ATAGGAGGGA
6451  AGGGATTAAG GGCAACCAGA GAGAGAGGGC CGAGAGAGCC GGGGCGCCTC
6501  TGGCCTCAGG GTGCATGAGA TAATGTAGAA TTTAAGCTCG GGGAGTCCAG
6551  CTCCAAGCTC TGGATTTGAA TCTTGACTCC ACCATCACTT TCCAGTTCTG
6601  TGGCCTCGGG TGGGTTACTG AATGTAAACC TGTCTCAGAG TTGTAAGGGT
6651  TAAATTAGAT AATGGGTATA AAGTGCTTCG CGCACTTAGT AAGCACGCAG
6701  TATATCTGAG CCCAGGGTGG GGGGACAGTG TTTGTGAGCT GTCAGCCACT
6751  GAACAACTGG TCACTTTGCA ACAACCGTAG GTTCAGAACA GCTAGTCCTT
6801  TACCTCCTCA CCCCATGGCC CTTCCTGCCC TGTCTTTCCA CATACACAAC
6851  AGCAGGGTGA TGGGCAGTTC TGGAACAAAC CAGAGCCCAG CACAGGGGCA
6901  CCTGGTAGGA CCCAGCACCC GGGAAGGCTG GACGATGGAG CACCACGGTT
6951  GCYTCTGGGT GCCTGGAACC CTGTCCCCAC CTCCAGTGGG AGTCCTGACC
```

Figure 1C

7001 TGGACATCTT CCCTCCAACT GGCTCTGCGW CCCCAAATGA ATCTCAGCTC
7051 CTAGAGAAGA CAGGAGGCCA TGGCCCTGGT GCCTTTATGG TCCTCTGTCT
7101 GAATGCTAAT CTCTTTACTG GCTGGAGCCT GAGTGACAGG GAAAAGGCGG
7151 TTCTGAGCTG CAGGGTGGCC GAGGGCGGCA GGMGGGAGCA GGGAGGTGCT
7201 GTTGTCTGCT ACTTCTGTGG CTGCTGCCAG TCTCTCCTRG AGATGGGAAC
7251 ATGACCAGAG AGCTAATGAG GTGGCGGGGG TGGGGGTGGG GGAGAAAGGG
7301 AGGCAGACGG AGCAGCTGCA GCAGCTGCCA CTGCCCTGTG TCACCCCAGG
7351 GTGCAAATGC CACCACGGGG AGCACCCCGC CCATCCCGAA CTGTGTGGCT
7401 GTGCAGATGC GGGCAGGATG GTCCTGGGCA CAGGCCTTGG TCCAAGACCA
7451 GGCAGGCGTG GTACTTGATC TGAGGTGGGC ATCATGGCAC AGGAGCTGGT
7501 CCCAGGGGTG CCCGGGGACC TTTATAGAAC CTCAGTCGGG AAGAAGCCCA
7551 AGACCTTGAG CCAGAGGGAA GTAATGCTTC TTTGTGAGCC TCAAAAGGAG
7601 GGAAATGGCC AAGGTTTACA GTAATATAAT GACACTAATA TTATTATTAA
7651 TAATGGCTAA TGTGTCTCAA ACGCTTCTTA CGTGCTAGGC GCTGTGCCAA
7701 GTGCTTTATT TATATGCATT GTCTCATTTA TGGGGCAGGA ACTGTTGTCA
7751 GTCTCATTTA CCCAATAAGG AAAGTGCTTG CTCAAGGTCA CCCACAGTGA
7801 GTAGTGAAGC CAGGACGTGT TCCCCGGCAA GGTGATGTAA AAGCCTGTGA
7851 AGGTRTTGGG CCTCGAGGAC ATCCTGGGAG TGTGACCTGT CCACCAGGGC
7901 ACAGGGCATG AGAGCTGGCA ACCCTCCCTG GTGATACTGC CGCTGCTCAG
7951 TCTGCAGAAA CTCATCATTC CAGGCTGGAC CAGACTCTGG GCCCCGAGGG
8001 CAGTGACCAG AGCCACCTTT CCAGGATCTG TCATGCTCCT CAGGGAGGAA
8051 GCAGTGGCCA CTGGCAGGGA TGACAGATAT CAAGGTTGTC ACTCATTGCT
8101 GCTGTTGCTC TGCTGTTTCC TCCAACCAGG GGCAGAGCCC TGGGGGTAAG
8151 GGAGGGTGGC AGCCAGCAGC CCAGCCAGAG AAGGAGGAGC CAGAGGAGGA
8201 AGGCTTTGTT GTTTGTTTTT ACAGGGGGAY GGTGCAGGGC TTTAAGGAGG
8251 TGGCTTCAAG ACCTGCTGAC TTTAGCCATA AACTGGTACC TAAGGGTGCT
8301 GGACCCTCTC TGTGGGATAC ATATGCCCCC TAGTGGGGAT TAAGCCTGGA
8351 GGGTGGCTGA GAAAATTAAA GCAAAACAAA ACAAAAAAAG ATTTACTGAT
8401 AGGCTATATG ACCTCCGAAC CTGGATAGGA AGGGCCAGGG CTGGCCCCCT
8451 GTGTCCCCGA GATTGCACAA GCACGCACAG GTTTAAGACA ATTTGCAGAA
8501 CCCAGGTGAA CGAAGCATTG AAAGAAATTA TTTAATTTAT TCCTTGGTCA
8551 TTTATTTAAG AAGCATGTAT CGGGAGCCTG TGATGTACAC ACCCTGTGGT
8601 AGGTGTTGGA GTCAGACAGC AATCAAAGGG ACGGCGCCCG ATGTGCCAAT
8651 GAGGACGACA GAAAGATCCT GGCCGAGGAG GCCAGTTGTG CAAGCTCAGC
8701 CGCTGCCTGC CACGACTTTT ACTTCTCTGG ACCTCAGTCT CCCCATGTAA
8751 TAGGCAGTGT TGAACCTAAG TGGGCTGGTG CAGAGGATGG GAAGGACCAC
8801 TGACTACCCT GGTAAAATGA AGGGGATGGA CTTCTTGACC TCGGGGGGGG
8851 CCCTTCCAGA TTCAAGACAG GCTACAGTGG ACAGTGTTTG GAGGTGCTGA
8901 CAACGGTGAC TCGCCCACTC AGCAAGCGTG TATGGAGCTC CTGTATGCCA
8951 GGCATTGTGG GTGGCAGAAA TGAAGCRCCC AGAAAACTGG ACAAAACTGA
9001 AGAAGCAACA GACACTTGAC TACAAGGAAC ATCCAAGATG GTGATCCCGT
9051 GACCACCTCA GCATCTACCT CCCACAGGTC CCTGCCTGAG CACAGGGAGG
9101 GGAAACCCAG AGGACTGCAG TGGTCTTGTT CAGCTGAGGA GACAAGATCA
9151 GAGCTCAGAA CAGTGTGCTG TTCCTAAAGA TATACACACA CATCAATGGC
9201 ATCTCCAAAA CAGACACAAC GAAGATGATC CAATGGAGAA AGAAAAGCCC
9251 TTTTGAGGAA ACACAAAAAG TGCTAACCAT AAAAGAAAAA AACAGATAAA
9301 TTGGACTTGA TCAAAATTCT TGGAAAGACT GGAAGAGAAT ACTAGCCAAG

Figure 1D

```
9351   CAAAAATCCG AACAAGGGCC TGTATCCAAA ATATATAAAG AACTTTTACA
9401   ACTCAATAAG AAGACGACAG CCCAACGGAA AAGTGGGGGA GGGTTTTAAT
9451   AGACACTTCG CAAGAAACTA GACATATGGC CAATAAACAC ATAAAAAGAT
9501   ACACAACATC CTAAGCCATC AAGGAAATGC AAATTAAAAC CACAATGAGA
9551   TACTACTGCA CACTCACCAG AATGGATAAA AGATGGACCA TAATAGACGT
9601   GGGTGAAGGT GTGGAGCAAC TTGTAACCCT GTCATACGTT GCTGGGAAAC
9651   CTGTTTGGCA GTTTCTTAGG ATGTAATCCA AGAGGAGTGA ACATGTAGGT
9701   CCACACAAAG ATTTGTACAG AGATGTTCAC AGCAGTGTTA TTATCAATAA
9751   TTAGTATCCA AACTGGAAAC AACGCAGATA GCCATCAAGA GGTAAATGGA
9801   TAAAAAAAAA AAAAAAAAAA AGGAGGCGGT GTATTCATAC AATGGAATAC
9851   GATTCAGCAA TAAAAAGGCA TTGAGCTACT ATGTGAGCCA TAACACAGGG
9901   CAATGAGAGA AGCCAGATGC TAAAGAGCAC CTACAGTATG AATCCATTTA
9951   TAGGAGATTC TAGAACAGGC AATAACTAAT CGGGAGTGGC AGAAAGCAGA
10001  TCAGTGGTTG CCCGGGGCCA GGGCTGGATA TGGACACTGT GAAATAGCAG
10051  GTTGGTACCC TCCAGGGGGA TGGAGATGTT CTAAATTGAG ACTGGGGTTG
10101  TGGTTTTATG GGTGTATCAC TGGCTGGACT ATTTTAAATG GATGCACTTT
10151  GTTATATGTA AATTATACCT CAATAAAGAT GACTTAAAGA GTTAAAAAAA
10201  AAAAAAAAAA AAAGAACCAC GAGAATGAAR ACCTGATCCT TGTCTTGCTT
10251  ACAGTCTAGT GAAAACGMCA GATGTGAAAA CAAACAACCA TAAGGCGGTG
10301  AGTAGCCTAA GAAGCATGCT CAAATAACAA GAGTTCTGTT TATGAAGGGC
10351  TCCCTCGCGC CAGACCCACA GAGGTGGCTT GGCGTCACTG TTCTAGAAGT
10401  CCAGATAAGA AAAGAGGCTG AGATGGAGGG GAAGTTGTTC ACGCAGGATT
10451  ACTCAGCTAG AATCAGCAGG CCTGGGACTG GGCTCCAAGG CTGCCTGGGT
10501  TCAGAGCAGG TGCCACAGCA GCCTGTGGCA GGACACCGAG CAGAGAGCTC
10551  GGGACTGTTG CAGCTTCTCA GGTGAGACTT TGCGGAGGAG GTATTGACAC
10601  AGGAGTTGGA ATTTGCTCAG CAGAGTAGAG GATGCGGGGA AGGAAATTTC
10651  AAAGCAAAGG GAACAAACAA TATGAGCAAA GGCTGGGCAA CACTTGTGAG
10701  AAGGCAGGGT TCCTGGGAAT GGAGAGACGT GTCCCGAAAA GAGCAGAAGA
10751  GGTCAACAGG ATATTACATG TTCTTCGCAT TCACTTATTT TTTTAAGAAC
10801  CTATTAAGCA ATAATTTTTA CGAGAGGCAA CAGCTCTGCA GGGCAGGCAA
10851  GTGAWGTATG TGCTCTTGGC AAACGCAGGG AAGAACCCAC CGTGATGCCA
10901  AGGTTGCCTC TTTAGGGAAA GGGGTTCTCC CTGTGACATT TCTCCTCCTC
10951  CAGGAGGTTA AGGCTGTGTT CCAGGATCCC AGGTTTCTGC TGAACACCCT
11001  TTGTGGCACT CTTTCACGGT CCTGAGAAAT CCCAGGAGGA AAAAAAAAAA
11051  AACAAAAACC CGCCTGTGCT TTTATGCTGG GCTTTCTGGC TGGAGGAAGT
11101  CAAGTCACTG GAGCGAAGCA AAATGTGTCA CACTGTCATG GTGCGTTCTT
11151  CTGGAAACTC AGCACAGCAG TGAGGTTTGG AGGCTTTGAG GCTGGACTGG
11201  CTGAGGTCAG ATCTCAGCGC TCTTTCACAC TGATTACTTT CCCCTTTCTG
11251  CACTTTGGCT TCTTTAGAAG ATTGCAAAAG AGGGGTGATC ATAAGAGGGC
11301  AGATGTGAGA ATGAAGGGAC AGTACGTGCA ATGTGCTCAG TCAGACTCAT
11351  CGAGTCTGAG ACGTTAATTT AGCCTGTATA GCCTTTTGTA TGACAGTCAG
11401  TCCTCCATAA ATCAGTTTTT TAAAAAGAAG GTGCTTAGAG CAGAGCCTGG
11451  CCCAGAGCAA ACATTTAATA GACAGTAGCT TTTGTGTTTT CAAAAAGGTG
11501  ACATGCACAT GTCATCCCTT TTATTTTGCT GTGACCCGTT CTTTCAGAGA
11551  ATTATAATGA AGCGGGATTT GGGACATGTT GATCATATCA TTTAGGATGA
11601  TTGTGACTCT TAACAGAACA CCCAACTTAG GGTGGCTCAA ACAGGAAGGA
```

Figure 1E

```
11651  GATTTCTAAA TCTCACATTC TGGGGCGCCT GGGTGGCACA GTTGGTTAAA
11701  CATTCGACTC TTGGTTTTGG CTCAGGTCAT GATCTCAGGG TTGTGAGATG
11751  GGGCCCTGTG TTGGAGTCTG CGCTCAGCTC ACAATTCTCT CTCTCCTCCA
11801  CTTCTGCCCC TCCTGCCCTC TCTAAAATAA ACATTTGAGG GTTTTTTTAA
11851  AAAGATTTTA TTTAGTTAGT TGAGAGAGAG ACAGACAGAG ACAGAGAGAC
11901  AGAGAGTGAG CATGTGTGAG CACAGGTGGG GAAGGGCAGA GGGAGCAGCA
11951  GAATCCCTGC TGAGCAGGAA GCCCAACACA GGGCTTGATC CCAGGACCAA
12001  GATCAAGACC CGAGCCAAAG GCAGATGCTC ATCCAACTGA GCCAGCCAGG
12051  CAACCCTAAA ATAAATGTCT TTTTTTAAAA AATCATCCTG TGTTTCACTG
12101  AAACTAACAT GCCATTGCTT GTGAGATGCC CCTTGCATTC AGAAATATTA
12151  AAATATAAAA ATGTGTGTCT TTGARTTGAA ACAAAAGGTC TGAAGGTAGG
12201  GGGCTCTAGG ACTGGTAATT TGGCAGTTCA CCATGAGGAC TCTTTGTCCT
12251  TTGTTTCCAC TCTGCCATCG TCAGACCTTA GGCTCTGGCT TTGAGGCAAG
12301  CCTCATGGAT GCAAGATGGC TGCCAGGGCC TCAAGCATCA AGTCTTCAGA
12351  GCCTCCCAAA GCCAGAAGAG AGGCTGCTGT TTTTAAAAAC AAGAAAAACT
12401  TTCCCAAACT TTGCTTAATT GCATCACAAA CCCTTTTCTG AATTCCTGGC
12451  AGAAGGAATA GATTTATCAT AAGGGTCTGG TGCCGACTCT TCAAGATTCG
12501  CCCTTAGGGC CGGGGAGGAG CTTGCCTCCA CTGAAGCACC GAGCTCCAGT
12551  TCTGTTGTGA GATGGAGGAA GAACAGCTGT GAGCTGGCAA TGAGCAGCGC
12601  TGCCATACAG ATRAACCGCC TGTGAATCAC CGGTCAACTG TGCCCGACAG
12651  AAGCAGCTGA CTGCTTGGGA TATTCCTACC CACCTTCCTG TTCCTATCAA
12701  CAATGGTAGA GCTTCCTCTC CAGGTTAAGA AATTAACCTC CATATTCCAA
12751  AGACTTGGTT TCCTATTAAT GTGGCTTTCG GGTACCGTAT CCAAAATCCT
12801  ATCCGGATGG AACCCAGTGA GTTAGCCACC TGAGCACAGC AGGCCAATGG
12851  ACTAGATTTC ACCTCCGTGC TCAGAGCCAA GGCCCCCTGA CCGCACCGAG
12901  GACTGTGGCC TTGCTCAGCC TGGGATCTAC TTCTGTCACT GACCACTAGA
12951  TTGGGGGACT CCGTGTCAGT GAATACAGAT CCATGCTAGC CTAGGATGAC
13001  GGCTACGTAA CAATTCCACT GCACATAAAA ACTCAAGTGT CCCAGACCTC
13051  GGGGCGCCTG GCTGGCTTAG GGAGGACTGA CTCTTAATCT CAGAGTCTTG
13101  AGTTCAAGCC CTGTGTTGGG TGTGGAGCCT ACTTAAAAAA AAAAAGAAGA
13151  AGAAGAAGAA GGAGAAGGAG AAGGAGAAGG AGAAGGAGAA GGAGAAGGAG
13201  AAGGAGAAGA AGAAGAAGAA GAAGAAGAAG AAGAAGAAGA AGAAGAAGAA
13251  GAAAGAAGAA GAAGAAGAAG AAGAAGAATT AGAAATCACA ACATTGATGC
13301  TTTGATCTCC ACAGCTCTGA ACTCCCGCCT GCTCCTTCAG AAATCTGATG
13351  CGTTCTCTGT TGTCTTTCCA CTGATTTTTT TCTTTTTTTT TTAAGATTTT
13401  ATTTATTTGA CACACAGAGA GATCAGCAGG GGGAGCATCA GAGGGAGAGG
13451  GAGCAGCAGG CTCCCCGCTG AGCAGGAAGT CCAACATGGG GCTCAATCCC
13501  AGGACCCTGG GATCATGACC TCAGCCAAAG GCAGATGTTT AACCCACTGA
13551  GCCACCCAGG TGGCCCTGAT TTTTTTTTTA AGATTATTTA TTTATTTTAG
13601  GGATCCCTGG GTGGCGCAGC GGTTTACCGC CTGCCTTTGG CCCAGGGCGC
13651  AATCCTGGAG ACCTGGGATC GAGTGCCACA TCGGGCTCCC GGTGCATGGG
13701  GCCTGCTTCT CCCTCTGCCT ATGTTTCTGC CTCTCTCTCT CTCTCTGTGT
13751  GACTACAATA AATTAAAAAA TATTTTTTAA TATTATTTAT TTATTTTAAA
13801  ATATTTTATT TATTTATTCA TGAGAGACAC AGAGAGAGAG GCAGAGATAC
13851  AGGCAGAGGG AGAAGTAGGC TCCCACAGGA CTTGATCCCA GGACCCCAGG
13901  ATCACGACCT GAATCCAAGG CAGATGCTCA ACCACTGAGC CACCCAGGTG
```

Figure 1F

```
13951   TCCCATTAAA GATTATTTAT TTGACAGAGA GAGAGAGAGC AGGAGCAGAG
14001   GGGCACAGGG AGAAGAAGAC TTCCTGCTGA TCGAGGAGCC CGACATGGGG
14051   CTTGAACCTA GAACCCTAAG ATCATGACCC AAGTTGAAGG CAGATGCTTA
14101   ACCAATGGAG CCACCAGGTG CCCCATCCTC CCCTATTTCT GGACTGCCCA
14151   GGCAGTGTGC CCTCTGCCTG CCACTCTTCC TGCTTGTGTG CTCTATTTTT
14201   CAAATAAATA AATTAATTAA AAAATAATAA TCTTGAGGCA CCTGGGTGGC
14251   TCAGTGGTTG AACATCTGTC TTTGGCTCAG GGCGTGATCC TGGGGTCCTG
14301   GGATCGAGTC CCACATTGGG CTCCCTGGAT GGAGACTGCT TCTCTCTCTG
14351   CCTGTGTCTC TGCCTCTCTC TCTCTGTGTG TGTGTGTCTC TCATGAATAA
14401   ATAAATAAAA GGGATCCCTG GGTGGCACAG TGGTTTAGCG CCTGCCTTTG
14451   GCCCAGGGCG CGATCCTGGA GACCTGGGAT CGAATCCCAC GTCGGGCTCC
14501   CGGTGCATGG AGCCTGCTTC TCCCTCTGCC TATGTCTGGG ATCCCTGGGT
14551   GGCACAGCGG TTTGGTGCCT GCCTTTGGGC CAGGGCGTGA TCCTGGAGAC
14601   CCGGGATCGA ATCCCACATC GGGCTCCCGG TGCATGGAGC CTGCTTCTCC
14651   TTCTGCCTGT GTCTCTGCCT CTCTCTCTCT CTGTGTGACT ATCATGAATA
14701   AATAAATAAA ATCTTAAAAA AAAAATAAAT AAATAAAATC TTTTTATTAG
14751   ATTTTATTTA AATCTTTTTA TTAGATTTTA ATCTCACTGC GTTTTGCTCC
14801   GGCCTCTCGG CGCCTGCCCA GCCACCCGAG ACATGCCACC TGCGGTGAAC
14851   CTGCTGCTCT TCTACTAGGT GTCCTGTCAG GTGTGAAAGC TCCACTGTAG
14901   ACCGTGGCAT TGTGGCTCCT CTCAAGCCCA GAAGAATGCT CCATGCTCCT
14951   CACACGCACT AGCTGGCAAC CGGTCTGGGA CTCAAGACAG CCCTGCTAGA
15001   GCCCAGAGCC CCCCAGTCTT GCAGCCATCA GCYCCTGCAG CCTCTCCTCC
15051   TCACTCTGCT TGCCATAAAG TGGCTCAAAA CCACGGAACA GGTGCCCATC
15101   ATTCCCCTGA GTAATTTCAT CCCAACCACC CCTGCAAACA CACAAAACCC
15151   TTCTTTGCTC CTCTCCCCCA TGCCCAAAAG CCCTATAGTA AGACTGATGT
15201   ATAGATATAC GAAGTTCAGT ACATCTTAGT GGTGAGAGTA TGGACTCTGC
15251   AGGCTGGCCT CAAACCTTGA CCCCAGCAAT CACTAGTTGT GTGAATTTGG
15301   GAAAGTCACC TCATCTCTCA CTCACCTCAC CTCATCTGCG AAATGCRGGT
15351   AGTGATAGWG CCCTTCAGAG GGCAGCGGTG CACATTAAAC AAATTGGTGT
15401   GCGTTCAGTA CTCCAGGAGT GGACGGCGCA TGGTAAGTGC TACCYGGTAT
15451   CCACTCTCGC TGTTATTCGG CCTGCAGCGG GTCCCTTGCC TCCATCCAAG
15501   CAGCTCTGGG GAACTTCCAC ATTCAAAACT CCCTCTCCGA GTCTGAAAAT
15551   GAAAGGAACT TAGTTTTCAG GGAGAGAGCC CATTCCTCCT TTCCCTATTC
15601   TACAAAACTG TATTCAAGGG CAAGACAGAA ATGCAAGGGC CAGTTTCATA
15651   AGACAGATGT TACTGCCAAG TGAGTCAATG ATTATCTGTT GTGTACGTGG
15701   GCAGAGGCAG AGGAATAACA ACCAGACTCT GGGAGGCAAT TAAAAAGAAA
15751   AAAAAAAAAA GTAAAAGAGT GTCTCATGGA GCGCCTGGGT GGCTCAGTCC
15801   GTTAAGCCTT GGACTTTTGG TTTCCCCTCA GGTCATGATC TCAGGGTCGT
15851   GGGACCCAGC CCTGGGGCGG GCTCTGTGAT CAGTGGGGAG CCTGCTTGAG
15901   ATTCCCTCCT TCTGCTGTGC ACACTCTCTC TCTAAAATAA ATACGTCTTT
15951   AGAAGAGCAA GCGAGCGAGA GATGCTTCCC GCCTAGAAGA GCTTACAATC
16001   AAATCAAGGG AGGCAAACAT AAACAAGTGT GGCAACTTGA TAATAAGCAC
16051   CTGCGACCTA TGGCCATACA CAGAATAACA TAACCCAGAC TAAATGCCAC
16101   TGCATAGTCA CTAGCGGGTT GATGACAACG GGGGGAGGCT AATGCTGAAA
16151   AGGCCTTTCT GTCTTATAAG TTTAAACTAA TTTCTGGGGG CACCTGGGTG
16201   GCTCTGGTTG AGCATCTGCC TTTGGGTCGT CGTCCCAGGG TCCTGAGATC
```

Figure 1G

```
16251  GAGTCCCTCA TCCGGCTCCC AGCCCCGTAG GAGCCTGCTT CTCCCTCTGC
16301  CTCTTCCTCT CTGTCTCTCA TGAATAAATA AATAAAAATT TTAAGGGATG
16351  CCCGGGTGGC TCAGCGGTTT AGCGCCTGCC TTTGGCCCAG GGTGTGATCC
16401  TGGGGTCCCG AGATCGAGTC CCACATCGAG TCCCACATCG AGTTCCGGGA
16451  TCGAGTCCCT GCAGGGAACC TGCTTCTCCC TCTCCCTGTG TGTGTGTCTC
16501  TCTCTCTTTC TGTATCTCTC ATGAATAAAT AAAGAAAATC TTTAAAAATA
16551  AATAAATAAA AACAGTATTT AAAAAAATGA ACTAATTTCC AAGTAGGTGT
16601  AAATTCTGGC TCGGACTAGT GAATGGCTCT GGCTCTGCTG CATCACCCAC
16651  CGCCAGGGCT CTGGGCCGCT CCGAGCCCCG CTCGCCGGCG CCCCCTGCCG
16701  CCCGGGCCTC CCGCCTTCAC CCCAACCCGC AGGGCGGCGG AGCCCTAGGC
16751  CCAATCGGCC CCGGGAACCT GCCGCCTCTT CTCTAGCGCA ACCCAGCACC
16801  CAGATGACCC CTTTTCCGCC CCAGGTGCAG TCCGGCCGGG CCCTGGTGTC
16851  CTCACCCGTT CCCCTAGGGA GACCCCTCTC GAACCTTCTG CGCCACCCTA
16901  CTCTACGCCA GGGAAAATCT GTGCACTCAG TAGATAAATG CTTGTAACTG
16951  AAGCAACCGT CTCCGTGGCT CCAGAATCGC GCTGAGGATG CTGCTGCCGC
17001  ACCCCCACCT CCCCCGGCTC CGGCGGAGGT TGTTTGGACT ACACTTCCCA
17051  TGAGGCCCCT CTCAACATCG CGATAACTCT CGCGAGACCG CTGGGAAGAG
17101  TTGTGCGCAG GCGCAGCCCC GCCTTCTTGT CGAGGCAGGC CGCGTGGCCG
17151  GCAGTCATGG CGGCTCCTTG CTGGCCCGAC CGGGACAGGG AGTCTGGAGY
17201  CTCTGGCTGT GGTAAGGTTG TCGAGGCGGG CAGACGGGAT CGTCCTTGGC
17251  CCGGCGCTAG TTCGCTCGGC CTCCCTTTCC TCGGGGGCGG GATGATGACG
17301  GTAAAGCCGG TCTTCCTCGT AGGGTGGTTG GGTTAGTTGA GATGCTGGAT
17351  CGGAAAACGC TTTCTGAGCG GCGCGAGTGT TGACGATCGA AGGGAGAGAG
17401  CTCAGGCCCC CCTTGGAGTC AGAGGGCCCC TCCTGGGGGG GGGGGTCCTC
17451  CAGCCTGTGC AGCCCCGTGT GTGCCCTGCG GGTCTCCCGG GCCCGCCCAC
17501  GGGAGGCTGC CGGTGGTAGT TCTTAATCCA CATCAAGTGT TAACGTGAGG
17551  GTCCTGGAGT GCCCCGAGGT CGGCCCTGGT CAGTGGTTCG TATTCAGTCC
17601  TACAGATAGT AGTAAAGGGG CTTGTAGATT TGGAAAGCCC ATAATGCTCT
17651  GCGCCCTACC TTCCATGTTC ATTTTTTTTC CCCTCTCTCT TCCCGTACAG
17701  GGTTTTCTTT GCGTCGCAGA CCTGCAGGTT GAAGCTTAAA AGTAGCGAAT
17751  GGGGAGCCCT GTGAAATGGG TAAGGATGGG TGCTGGCAGG GCCCGGGTGG
17801  TGACCAGAAG TGAGAAAGTC GAGATGGTGG GCAGGCCTGC CACACCCGGC
17851  CGCCGCACGC TTTACTTTAC TAATTTTATT TTTTTTTAAA GRTTTAATTA
17901  ATTAATTAAT TAATGATAGG CAGAGACACA GGCAGAGGGA GAAGCAGGCT
17951  CCGTGCCGGG AGCCCGACGC GGGACTCCAG GATCGCGCCC TGGGCCAAAG
18001  GCAGGCGCCA AACCGCTGAG CCACCCAGGG ATCCCACTTT ACCGATTTTA
18051  AGTTCGGTTC TTAGGAACAC GTGGACGCAC GCATCCGGTT AGGGTGAGAA
18101  GAAAACGGAC CCGGGTCCTG GAAGCGAGCA GGGCCTTGCC AGTGTGACTC
18151  GGCGCCGCTA GGTGTCACTG TTTGGATTCA AACCGGTTGC CGCGCACGAG
18201  GTTGGCGGGG AGGCTTAGGA AATGGGCTTC GGTGGGGTTT GGAAGTATTT
18251  GTGGATGATT TAAAGTTATC TTTGTCTTAA AGGGCTCTTT TGTGAAGAGT
18301  TTTGATGCGT TGAGGCTCAG CTTTTTTTTT TTTTTTTTTT TAAGGTTTGT
18351  ATTCATTTTT TCACAGAGAG GCAGAGGGAG GAGAAGCTTG CTGCCTGCAG
18401  AGAGCAGGAT GCGAGACTCG ATCCCTGGAT TTCGGGATCA CGCCCAGAGC
18451  CAAAGGCAGA CACGCAACTA CTGAGCCACC CAGGCGTCCC GAGGCCCCAG
18501  CTTCTTAAAT AACCAATCTT GAGAATAACA TCTTGACCTC ATTTCTCTTA
18551  GAATATACTT TGTTACATTT CCCTTAGAGA TTAAAGGTGT TG
```

Figure 1H

```
  1  AGTGGCAGCA GGAACCTCAG GATGGGCAGC AGTGGCTTGT GAGAGCCGGC
 51  AGGGCCATTT TGGCCTTTCT CCTGCAGACT CTGTCCGGGA GGGGATGGGG
101  CAGCTGAGCC ATGTRCACCA CCCTCTTCCT ACTCAGCACC TTGGCCATGC
151  TCTGGCGCCG CCGGTTCGCC AACCGGGTCC AACCGGAGCC CAGCGGAGCA
201  GACGGGGCAG TCGTGGGCAG CAGGTCGGAG AGAGACCTCC AGTCCTCGGG
251  CAGAAAGGAA GAGCCTCTGA AGTAAGTCTT CACCCGGTCA GGCGGAGCTC
301  GGCCCCAGGG AYTGGGATCA GCTGGCAGAG GCAGTTCAAG TCCCGGCTGG
351  CCTCTTACCC ACAAAGCATG CTGTGGTGGA AGCAGCAGCA GCAGCAAGAA
401  GAAAAATGGG AAAAAGCAGT CATCAAGAAG GTAGACTCCT CCCTTTGAGT
451  CCCTGGACCT GCCTGGCCTC CCTTTGCCCC AGACCCTGGT GGTGGGGCTC
501  CTGAAGCAAG GCCTGGCTGG GGCAGGCTGG AGGGCAAAGA CGCTCATTGC
551  CCTGGCTTGG GCTCCCTTCC TCTGAGATCC TGAGGATAGT CTGAGGCAGG
601  CCCAGAGAGG GACTCAGGTT TCTTATGGAA GGRCTTCTCA TTCATCCCTA
651  ATATAATCCT TGCAATGACC CAAAAAAAAA AAAAAAAAAA AAAAA
```

Figure 2

IDENTIFICATION OF THE GENE AND MUTATION RESPONSIBLE FOR PROGRESSIVE ROD-CONE DEGENERATION IN DOG AND A METHOD FOR TESTING SAME

This application is a Divisional of U.S. application Ser. No. 11/157,743, filed on Jun. 21, 2005, now U.S. Pat. No. 7,312,037 which in turn claims priority to U.S. provisional application No. 60/581,499, filed on Jun. 21, 2004, the disclosures of which are incorporated herein by reference.

This work was supported by Grant No. EY006855 from the National Institutes of Health (NIH). The Government has certain rights in the invention.

FIELD OF THE INVENTION

The present invention relates generally to a class of genetic diseases, observed in canines, termed progressive rod-cone degeneration ("prcd"). More particularly, the invention relates to a gene and a single nucleotide mutation in the gene associated with progressive rod-cone degeneration in dogs.

BACKGROUND OF THE INVENTION

Progressive Retinal Atrophy (PRA) is a heterogeneous class of retinal disorders that share a broadly similar clinical disease phenotype, and affect the dog (*Canis familiaris*) (Aguirre, 1976). The clinical features include: initial night blindness followed by reduction in photopic vision leading to complete blindness; reduction in retinal vessels, and retinal thinning; abnormalities in an electroretinogram ("ERG"); and the development of cataracts. Diseases of this group are typically inherited by means of an autosomal recessive gene defect although dominant and X-linked forms of PRA also are recognized (Kijas et al., 2002; Zhang et al., 2002). PRA may be classified into developmental and degenerative diseases. The developmental class comprises several genetically distinct diseases expressed cytologically in the immediate postnatal period when visual cells in the canine retina begin to differentiate (Acland et al. 1989). In contrast, the degenerative class represents defects in which photoreceptor cells degenerate after having differentiated normally—this class includes the specific disease termed progressive rod-cone degeneration (prcd). This specific form of PRA is an autosomal recessively inherited, late-onset retinal degenerations affecting several different breeds of dog (Aguirre and Acland, 1988).

Mutations at the prcd 'gene locus account for all of the autosomal recessive late-onset hereditary retinal degenerations recognized to date in dogs. By cross-breeding experiments, it has been determined that the prcd gene locus is responsible for progressive retinal atrophy in poodles (toy, and miniature), cocker spaniels (American, and English), Labrador retrievers, and Portuguese water dogs (see, e.g., Aguirre and Acland, 1988, Aguirre and Acland, 1991; Pearce-Kelling et al., 2002). Cross-breeding experiments suggest the same mutation in the F04 gene (which is gene responsible for prcd) is also present in several other breeds either in dogs affected with prcd; or carriers of the disorder. However, based on clinical and genetic parameters consistent with disease caused by mutations at the prcd gene locus, other breeds of dogs suspected of having prcd as the form of observed progressive retinal atrophy include akita, basenji, border collie, English mastiff, English springer spaniel, Havanese, lowchen, samoyed, standard wirehaired dachshund, Tibetan terriers, Bernese mountain dog, and miniature schnauzer. Depending on the breed of the dog, different mutations responsible for allelic variants of the prcd gene locus can regulate the rate of progression, but not the phenotype, of photoreceptor degeneration.

Clinical diagnosis of prcd disease is complicated by the need for sophisticated testing methods such as ERG, and by the late onset of the disease. The age at which the disease can be diagnosed by current methods may be past the dog's reproductive life. For example, in English cocker spaniels, progressive retinal atrophy may be diagnosed by ERG at three years of age, and by opthalmoscopy at 5-8 years of age. This late age of diagnosis results in the dissemination of the undesirable trait within the population, and an increase in the disease frequency.

The estimated prevalence of progressive rod-cone degeneration differs among affected breeds. It is believed that approximately 2% of Labrador retrievers more than 2 to 3 years old are affected with progressive rod-cone degeneration; if so, then the proportion of Labrador retrievers expected to be heterozygous at the prcd locus could be as high as 24%. In poodles and cocker spaniels, the disease rate is higher than that observed in Labrador retrievers, and hence, the carrier rate would be expected to be higher. From the results of a survey of Portuguese water dogs, the calculated carrier frequency is approximately 40%.

Traditional measures for controlling inherited diseases in a population included performing "test" matings to identify carrier dogs, and to eliminate the identified carriers from breeding programs, thereby reducing the frequency of genetic disease in a breed. In a test mating, the dog being evaluated as a potential carrier of the genetic disease is mated with a dog known to be affected with the disease. Progeny are then observed for absence or presence of the disease, and a litter equal to or larger than 6, all of which are unaffected offspring, typically "clears" the dog from being a carrier. While test matings have been effectively used for breeds having large litter sizes, and for diseases which are early onset, such a procedure is not practical for reducing the frequency of prcd. In addition to the disadvantages of test matings such as great expenses in time and effort incurred to clear a dog and that affected dogs can be born if the dog to be evaluated is a carrier, test matings are not particularly suited for detection of carriers of prcd because of the late onset of clinical symptoms associated with the disease, and because some of the breeds affected have small litters (too small for establishing statistical probability).

Although the gene carrying the mutation or mutations that cause prcd has previously been unknown, genetic linkage studies in prcd families have shown that the gene that causes the disease in dogs resides on the centromeric end of canine chromosome 9, an area that is homologous to the telomeric end of the long arm of human chromosome 17 (Acland et al., 1999; Sidjanin et al., 2003).

In spite of the extensive efforts in the art to find the gene responsible for prcd, until now the gene has remained elusive. Identification, isolation, cloning, and sequencing of the prcd gene would enable the design and manufacture of products useful for the diagnosis and screening for prcd. Therefore, there has been an ongoing need in the canine breeding industry for a genetic test that permits direct identification of dogs that have the prcd form of progressive retinal atrophy (e.g., before detectable onset of clinical symptoms), as well as permitting the genotyping of dogs at risk for prcd to establish if they are affected, carriers or genetically normal.

SUMMARY OF THE INVENTION

The present invention provides an isolated nucleic acid molecule encoding a novel disease-associated canine gene, referred to herein as the F04 gene. The invention further provides the F04 gene having a G to A mutation at position 1298 of SEQ ID NO:1. This transversion is associated with and is indicative of prcd.

The present invention also relates to a method for identifying dogs, which are genetically normal, carriers of, or affected with prcd disease. Genetically normal dogs are those in which both alleles of the F04 gene have G as the nucleotide at a position corresponding to nucleotide position 1298 of SEQ ID NO:1. Affected dogs or predisposed dogs are those in which both alleles of the F04 gene have A as the nucleotide at a position corresponding to nucleotide position 1298 of SEQ ID NO:1. Carrier dogs are those in which one allele of the F04 gene has G and the other allele has A as the nucleotide at a position corresponding to nucleotide position 1298 of SEQ ID NO:1. A change of G to A in the F04 gene at a position corresponding to nucleotide position 1298 of SEQ ID NO:1 is termed herein as the "prcd mutation". The nucleotide position 1298 in SEQ ID NO:1 also corresponds to nucleotide position 115 in the cDNA sequence shown in SEQ ID NO:3

The method comprises the steps of obtaining a biological sample from a dog and testing the biological sample to identify whether or not G is present at a position corresponding to nucleotide position 1298 of the F04 gene. In one embodiment, the method comprises detecting a G to A mutation at a position corresponding to nucleotide position 1298 of SEQ ID NO:1 in one or both alleles which is indicative of a dog that is a carrier of or a dog that is affected with (or predisposed to) prcd respectively.

The present invention also provides a method for selecting dogs for breeding. This method comprises obtaining a biological sample from a dog, testing the biological sample for the F04 gene having a prcd mutation in one or both alleles, and eliminating dogs with the prcd mutation from a breeding stock, or breeding the dogs with the prcd mutation with genetically normal dogs.

BRIEF DESCRIPTION OF THE FIGURES

FIG. 1 shows the genomic sequence of the canine F04 gene.

FIG. 2 shows the sequence of the cDNA from the canine F04 gene.

FIG. 3 is a representation of restriction endonuclease digestion of amplified products from genetically normal, carrier dogs or dogs affected with prcd.

DESCRIPTION OF THE INVENTION

Figures 3A, 3B:
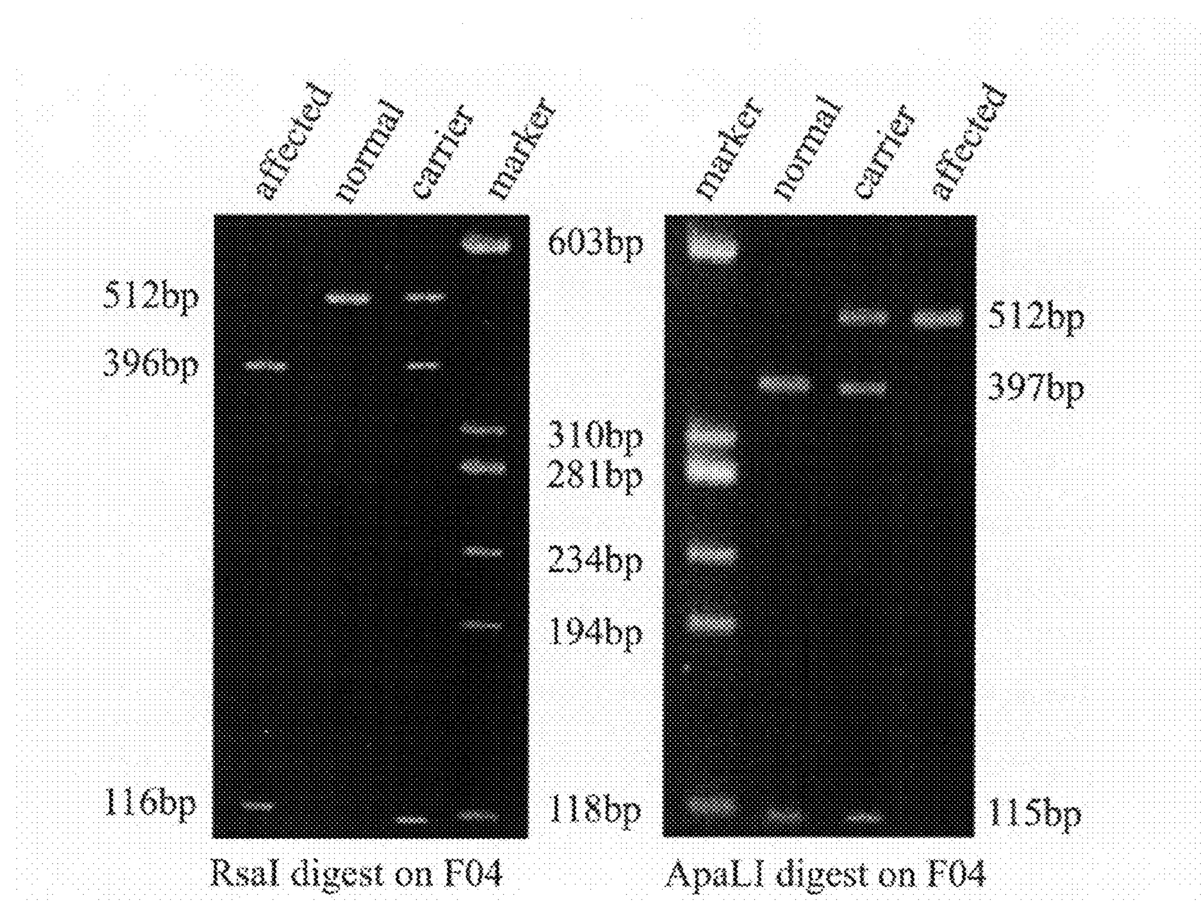
FIG. 3A shows digestion with the restriction endonuclease RsaI and FIG. 3B shows digestion with restriction endonuclease ApaLI.

This invention provides a nucleic acid molecule encoding a novel F04 gene located on chromosome 9 in dogs. The sequence of the wild type F04 gene is presented in FIG. 1 and details pertaining to the sequence are as follows.

Explanation of the Genomic Sequence

The genomic sequence of the F04 gene is 18592 bp long. The sequence listed in SEQ ID NO:1 includes, all polymorphisms identified heretofore. Nucleotide exchanges are shown in italics as follows: W=A/T; M=A/C; R=A/G; Y=C/T; S=C/G; K=G/T. Insertion/deletions are shown in italics and underlined. Sequence for the affected and alternative allele for all polymorphisms shown in the sequence are presented in a separate Polymorphism table (Example 2). Microsatellite at position 13,146-13,278 bp is also shown in italics and is boxed.

In the public domain canine genome sequence assembly (canFam1) dated July 2004 (http://genome.ucsc.edu/cgi-bin/hgTracks?org=Dog&db=canFam1&hgsid=42443361), the F04 genomic sequence (SEQ ID NO:1) is localized incorrectly to chr18:26,568,308-26,586,788. We believe this is incorrect, as we have established through our BAC contig, and by FISH and meiotic linkage mapping that, as predicted by comparison to the homologous regions of the human and mouse genomes, this canine genomic region is properly located on CFA9. This discrepancy does not affect the accuracy or the utility of the tests described herein.

Throughout this sequence, proposed exons and UTR regions are shown in upper case letters and defined exons are bolded. Intronic regions are in lower case letters.

Exon 1: bp 1-1,367

Includes a TATA box at position 727-731, three CRX binding sites at positions 1,122-1,128; 1,159-1,165; 1,177-1,183 and the ATG signal indicating the start of the ORF at position 1,294-1,296 all underlined and boxed.

The prcd mutation at position 1,298 is shown in italics, bold and boxed. The mutation is a change of G to A and is shown as "R".

Exon 2: bp 1,650-1,718

Exon 3: bp 3,746-3,826

Includes the stop codon at position 3,765-3,767 shown underlined and boxed.

Exon 4: bp 4,161-4,256

3'UTR: bp 4,257-18,592

Within this region there are several potential adenylation signals which are pointed out underlined and boxed. The region entitled 3'UTR has also been shown to contain regions of alternative splicing (indicated in bold), which further defines within this region:

Exon 5a: bp 4,806-5,399

Exon 5b: bp 4,839-5,399

Exon 5c: bp 5,093-5,399

Exon 6: bp 6,558-6,665

Exon 7: bp 6,927-7,164

Exon 8: bp 7,547-7,720

Exon 9: bp 12,275-18,592

The deduced amino acid sequence of a putative protein encoded by the F04 gene, based on the sequence of SEQ ID NO:1, and assuming a start site at position 1294 is shown below as SEQ ID NO:2.

Met Cys Thr Thr Leu Phe Leu Leu Ser Thr Leu Ala Met Leu Trp Arg Arg Arg Phe Ala Asn Arg Val Gln Pro Glu Pro Ser Gly Ala Asp Gly Ala Val Val Gly Ser Arg Ser Glu Arg Asp Leu Gln Ser Ser Gly Arg Lys Glu Glu Pro Leu Lys—(SEQ ID NO:2)

In this case, the prcd mutation would result in cysteine (the 2nd amino acid) being replaced by tyrosine.

The F04 cDNA Sequence (see SEQ ID NO:3)

Several splice variants of the F04 gene have been identified, all of which include the same ORF. The shortest full length splice variant is 695 bp long; the cDNA (SEQ ID NO:3) for this variant of the F04 gene is shown in FIG. 2. Those skilled in the art will recognize that potential future identification of additional exons, that do not alter the F04 ORF as described herein (such as a noncoding exon 5' to exon 1, or 3' to exon 3), will not affect the demonstrated association of the prcd mutation with PRA or detection of the prcd mutation as described herein.

Explanation of the cDNA Sequence:

The cDNA sequence embeds the ORF of 165 bp, located at position 111-275 (both start and stop codon are highlighted in bold). The mutation is located within the ORF at position 115 shown in italics, bold and boxed (Normal allele=G; mutant allele=A). Other polymorphisms (for examples: Y=C/T, nt 312 SEQ ID NO:3, Polymorphism# 55, Table 1; and R=G/A, nt 633 SEQ ID NO:3, Polymorphism# 57, Table 1) in the 3'UTR are not disease associated because both alleles have been identified on normal chromosomes. All cDNAs that include the F04 ORF incorporate exon 1 (bp 1-184), exon 2 (bp 185-253), exon 3 (bp 254-334) and exon 4 (bp 335-695), however, partial cDNAs obtained using different primer sets establish that different splicing variants in the 3'UTR can include at least exons 5 and 8 as defined in the genomic sequence. Other features are the same as in the genomic DNA.

Detection of the prcd mutation in the F04 gene can be carried out in any suitable biological sample obtained from a dog. In a preferred embodiment, the biological sample is any tissue containing genomic DNA. Suitable sources of biological sample include blood, hair, mucosal scrapings, semen, tissue biopsy, or saliva. In one embodiment, the biological sample is blood.

Dogs carrying the prcd mutation in F04 gene may be detected by testing either the DNA or the RNA, using a variety of techniques that are well known in the art. The genomic DNA used for the diagnosis may be obtained from a biological sample as described above. The DNA may be used directly or may be amplified enzymatically in vitro through use of PCR (Saiki et al., Science, 239:487-491 (1988)) or other in vitro amplification methods such as the ligase chain reaction (LCR) (Wu and Wallace, Genomics, 4:560-569 (1989)), strand displacement amplification (SDA) (Walker et al., PNAS USA, 89:392-396 (1992)), self-sustained sequence replication (3SR) (Fahy et al., PCR Methods Appl., 1:25-33 (1992)), prior to mutation analysis. The methodology for preparing nucleic acids in a form that is suitable for mutation detection is well known in the art.

Detection of DNA sequence mutations, such as the prcd mutation in the F04 gene, can be accomplished by a variety of methods including, but not limited to, restriction-fragment-length-polymorphism detection based on allele-specific restriction-endonuclease cleavage (Kan and Dozy Lancet, 2(8096):910-912 (1978)), hybridization with allele-specific oligonucleotide probes (Wallace et al., Nucl Acids Res., 6:3543-3557 (1978)) including immobilized oligonucleotides (Saiki et al., PNAS USA, 86:6230-6234 (1989)) or oligonucleotide arrays (Maskos and Southern, Nucl Acids Res., 21:2269-2270 (1993)), allele-specific PCR (Newton et al., Nucl Acids Res., 17:2503-2516 (1989)), mismatch-repair detection (MRD) (Faham and Cox, Genome Res., 5:474-482 (1995)), denaturing-gradient gel electrophoresis (DGGE) (Fisher and Lerman et al., PNAS USA., 80:1579-1583 (1983)), single-strand-conformation-polymorphism detection (Orita et al., Genomics, 5:874-879 (1983)), RNAase cleavage at mismatched base-pairs (Myers et al., Science, 230:1242 (1985)), chemical (Cotton et al., PNAS USA, 85:4397-4401 (1988)) or enzymatic (Youil et al., PNAS USA, 92:87-91 (1995)) cleavage of heteroduplex DNA, methods based on allele specific primer extension (Syvanen et al., Genomics 8:684-692 (1990)), genetic bit analysis (GBA) (Nikiforov et al., Nuci Acids Res., 22:4167-4175 (1994)), the oligonucleotide-ligation assay (OLA) (Landegren et al., Science, 241:1077 (1988)), the allele-specific ligation chain reaction (LCR) (Barrany, PNAS USA, 88:189-193 (1991)), gap-LCR (Abravaya et al., Nucl Acids Res., 23:675-682 (1995)), and radioactive and/or fluorescent DNA sequencing using standard procedures well known in the art.

Further, several new techniques have been described including dynamic allele-specific hybridization (DASH), microplate array diagonal gel electrophoresis (MADGE), Pyrosequencing™, the TaqMan system as well as various DNA "chip" technologies such as the Affymetrix polymorphism chips. These methods require amplification of the target genetic region, typically by PCR. Still other newly developed methods, which may not need PCR are based on the generation of small signal molecules by invasive cleavage followed by mass spectrometry or immobilized padlock probes and rolling-circle amplification. Several of the methods known in the art for detecting specific single nucleotide polymorphisms are described in U.S. Pat. No. 6,720,141 and the description of these methods is incorporated herein by reference.

As will be appreciated, the mutation analysis may also be performed on samples of RNA by reverse transcription into cDNA therefrom.

Any one or any combination of such techniques can be used in accordance with the invention for the design of a diagnostic device and method for the screening of samples of DNA or RNA for prcd gene mutation of G to A at a position corresponding to nucleotide position 1298 of SEQ ID NO:1 of the F04 gene. Thus, in accordance with the invention, there is provided a nucleic acid based test for prcd gene mutation which comprises providing a sample of a dog's DNA or RNA and assessing the DNA or RNA for the presence of the prcd mutation. Samples of dog DNA or RNA (or genomic, transcribed, reverse transcribed, and/or complementary sequences to the prcd gene) can be readily obtained. Through the identification and characterization of the F04 gene as taught and disclosed in the present invention, one of ordinary skill in the art can readily identify the genomic, transcribed, reverse transcribed, and/or complementary sequences to the prcd gene sequence in a sample and readily detect differences therein.

Accordingly, in one embodiment, the present invention provides nucleic acid fragments for detection of nucleic acids wherein the mutation is present. In general, the detection methods are based on DNA hybridization techniques, wherein hybridization to DNA sequences is performed under stringent conditions such that a change in one nucleotide can be detected. Optimal stringency is normally obtained by adjusting the reaction temperature and/or salt concentration so that the probe will only hybridize to its specific target, although those skilled in the art will recognize that alternative methods of optimizing for target specific hybridization are readily available.

Thus, allele-specific probes can be hybridized under conditions that are sufficiently stringent so that there is a significant difference in the intensity of the two alleles. Preferably, the hybridization conditions are sufficiently stringent so as to produce an essentially binary response (i.e., the probe hybridizes to one but not the other allele).

Further, primers can be designed which hybridize to a target sequence such that upon amplification, products are generated which contain the prcd mutation site. The primers should be long enough to be useful in reactions such as polymerase chain reaction (PCR) process or as probes in a ligase chain reaction (LCR) procedure. Generally fragments which are at least twelve bases in length are considered suitable for amplification reactions. The amplification products can be subjected to restriction endonuclease treatment and identified by denaturing gradient gel electrophoresis so as to distinguish between the amplification products from the two alleles.

Suitable fragments useful for hybridization can be identified from the sequence of the F04 gene presented herein or may be identified by hybridization to the nucleic acid sequence of the F04 gene (SEQ. ID. NO:1) or the cDNA (SEQ ID NO:3) under stringent conditions as described above.

By using the tools and method described herein, dogs which are genetically normal for the disease (G in both alleles), carriers of the prcd disease (G to A transversion in one allele) and dogs which are affected by (or predisposed to) progressive rod-cone degeneration (G to A transversion in both alleles) can be identified. Upon identification, such affected (or predisposed) or carrier dogs can be eliminated from the breeding stock. Alternatively, dogs which are affected (or predisposed) with prcd, or carriers of the prcd disease, can be mated with genetically normal (without the G to A transversion) dogs to ensure the absence in the litter of dogs affected with prcd.

This invention can be used for any breed of dog including, but not limited to, akita, American cocker spaniel, American eskimos, Australian cattle dog, Australian stumpy tailed cattle dog, basenji, Bernese mountain dog, border collie, Chesapeake bay retriever, Chinese crested, English cocker spaniel, English mastiff, English springer spaniel, Entlebucher mountain dog, Finnish lapphund, German shorthaired pointer, giant schnauzer, Havanese, Labrador retrievers, lowchen, miniature poodle, miniature schnauzer, Nova scotia duck tolling retriever, Portuguese water dogs, samoyed, silky terrier, spitz, standard poodle, standard wirehaired dachshund, Tibetan terriers, toy poodle. Because the identical prcd mutation in the F04 gene has been demonstrated to be present in, and cause PRA in so many different breeds, this mutation appears to have arisen long before the differentiation of the dog population into these different breeds. It is thus expected that the same mutation will prove to be present in other breeds of dogs in which its presence is not currently recognized.

The invention will be further understood by the following examples, which are intended to be illustrative and not restrictive in any way.

EXAMPLE 1

We have produced a retina specific canine EST library from 16 week old beagles. One set of 5 individual overlapping EST clones formed a contig which mapped to the previously specified CFA9 area (Sidjanin et al., 2003) and was therefore further investigated. This sequence contained the later defined F04 exon 8 (see below, EST clone contig, 1085 bp).

From sequence information from the above EST contig, and that of hypothetical human genes located within the corresponding region of the human genome sequence as deposited in GenBank, two primers were designed for RT-PCR: Forward: 5'-caccttggccatgctctggc-3' (located at the end of exon 1)—SEQ ID NO:4 Reverse: 5-aatgcatataaataaagcacttggc-3' (located in exon 8)—SEQ ID NO:5

RT-PCR was performed from a 3.3 week normal dog resulting in a 707 bp product (clone 9) spanning the end of exon 1, exon 2, exon 3, exon 4 and exon 8.

Comparative in silico analysis of canine genomic sequence from our BAC contig (see example 2, below), with public domain human and mouse genomic sequence, identified a highly conserved region, contiguous with the 5' end of clone 9, that included potential CRX binding sites followed by an ATG translation initiation codon immediately upstream to the sequence of clone 9, and predicted an ORF commencing with this ATG and ending with a stop codon in exon 3. This ORF sequence did not correspond to that of any known gene in Genbank, nor did its putative translation share recognizable domains with or sequence similarity to any other known protein in Genbank.

Because the F04 clone was identified from our retina-specific library, these data combined indicated that the ORF corresponding to F04 represents a novel, previously unrecognized, retina expressed gene. The presence of binding sites for the CRX photoreceptor-specific transcription factor, and the highly conserved structure of the region 5' to the identified start codon identified the putative exon 1 as the first coding exon of a retina-expressed gene. Based on this information a new primer set was designed to include the potential start codon and span exons 1-4:

Forward: 5'-ccagtggcagcaggaacc-3' (5' of exon 1)—SEQ ID NO:6

Reverse: 5'-ccaagccagggcatgagc-3' (3' of exon 4)—SEQ ID NO:7

RT-PCR was performed on both, an 10.4 week normal animal and an 8.6 weeks prcd affected individual resulting in a 562 bp product in both animals (see below, RT-PCR exon 1-4). The only difference observed was a G to A change observed in the affected individual which consequently was identified as the prcd mutation.

To identify the 5' and 3' ends of this gene, we created a 5' RACE retina library from a 10 week old normal dog and a 8 week old affected dog. Amplification of the 5' ends was done with different specific primers located in exon 1 (CCAAGGTGCTGAGTAGGAAGAGGGTGGTG—SEQ ID NO:8). or exon 3 (AGTCCCTGGGGCCGAGCTCCGCCTGAC—SEQ ID NO:9). Amplification of the 3' ends was done using a specific primer located on exon 1 (CACCACCCTCTTCCTACTCAGCACCTTGG—SEQ ID NO:10) which is the exact complement sequence of the specific primer that is used to run the 5' RACE. Seminested PCR was done with a primer located on exon 3 (AGGGACTGGGATCAGCTGGCAGAGGCAG—SEQ ID NO:11) to verify specificity of the product.

The consensus sequence from these experiments is the clone we consider as the cDNA for the F04 gene (see Seq ID No:3) which is shown in FIG. 2. Details of the cDNA sequence are provided above.

To validate the consensus sequence predicted from the 5' and 3' RACE, two primers were used to amplify the consensus sequence from affected and non-affected retina cDNA.

```
5'-AGTGGCAGCAGGAACCTCAGG-3'          SEQ ID NO: 29
5'-GGATTATATTAGGGATGAATGAGAAG-3'     SEQ ID NO: 30
```

Since the results of a 5' RACE and a 3' RACE are independent results this step is necessary to prove that this transcript is present in the affected and non-affected Retina. The RT-PCR confirmed the presence of such transcript.

By the method described above, the following sequences were obtained.

EST Clone Contig:

The clones originally contained in the EST library produced the following consensus sequence from 5 clones; 1085 bp:

SEQ ID NO: 12

```
GAGCAGCTGCAGCAGCTGCCACTGCCCTGTGTCACCCCAGGGTGCAAATG
CCACCACGGGGAGCACCCCGCCCATCCCGAACTGTGTGGCTGTGCAGATG
CGGGCAGGATGGTCCTGGGCACAGGCCTTGGTCCAAGACCAGGCAGGCGT
GGTACTTGATCTGAGGTGGGCATCATGGCACAGGAGCTGGTCCCAGGGGT
GCCCGGGGACCTTTATAGAACCTCAGTCGGGAAGAAGCCCAAGACCTTGA
GCCAGAGGGAAGTAATGCTTCTTTGTGAGCCTCAAAAGGAGGGAAATGGC
CAAGGTTTACAGTAATATAATGACACTAATATTATTATTAATAATGGCTA
ATGTGTCTCAAACGCTTCTTACGTGCTAGGCGCTGTGCCAAGTGCTTTAT
TTATATGCATTGTCTCATTTATGGGGCAGGAACTGTTGTCAGTCTCATTT
ACCCAATAAGGAAAGTGCTTGCTCAAGGTCACCCACAGTGAGTAGTGAAG
CCAGGACGTGTTCCCCGGCAAGGTGATGTAAAAGCCTGTGAAGGTATTGG
GCCTCGAGGACATCCTGGGAGTGTGACCTGTCCACCAGGGCACAGGGCAT
GAGAGCTGGCAACCCTCCCTGGTGATACTGCCGCTGCTCAGTCTGCAGAA
ACTCATCATTCCAGGCTGGACCAGACTCTGGGCCCCGAGGGCAGTGACCA
GAGCCACCTTTCCAGGATCTGTCATGCTCCTCAGGGAGGAAGCAGTGGCC
ACTGGCAGGGATGACAGATATCAAGGTTGTCACTCATTGCTGCTGTTGCT
CTGCTGTTTCCTCCAACCAGGGGCAGAGCCCTGGGGGTAAGGGAGGGTGG
CAGCCAGCAGCCCAGCCAGAGAAGGAGGAGCCAGAGGAGGAAGGCTTTGT
TGTTTGTTTTTACAGGGGGACGGTGCAGGGCTTTAAGGAGGTGGCTTCAA
GACCTGCTGACTTTAGCCATAAACTGGTACCTAAGGGTGCTGGACCCTCT
CTGTGGGATACATATGCCCCCTAGTGGGGATTAAGCCTGGAGGGTGGCTG
AG:AAATTAAAGCAAAAAAAAAAAAAAAAAAAAA
```

Clone9:

Produced by RT-PCR using primers from exon 8 and the end of exon 1 (707 bp):

SEQ ID NO: 13

```
CACCTTGGCCATGCTCTGGCGCCGCCGGTTCGCCAACCGGGTCCAACCGG
AGCCCAGCGGAGCAGACGGGGCAGTCGTGGGCAGCAGGTCGGAGAGAGAC
CTCCAGTCCTCGGGCAGAAAGGAAGAGCCTCTGAAGTAAGTCTTCACCCG
GTCAGGCGGAGCTCGGCCCCAGGGACTGGGATCAGCTGGCAGAGGCAGTT
CAAGTCCCGGCTGGCCTCTTACCCACAAAGCATGCTGTGGTGGAAGCAGC
AGCAGCAGCAAGAAGAAAAATGGGAAAAAGCAGTCATCAAGAAGGTAGAC
TCCTCCCTTTGAGTCCCTGGACCTGCCTGGCCTCCCTTTGCCCCAGACCC
TGGTGGTGGGGCTCCTGAAGCAAGGCCTGGCTGGGGCAGGCTGGAGGGCA
AAGACGCTCATTGCCCTGGCTTGGGCTCCCTTCCTCTGAGATCCTGAGGA
TAGTCTGAGGCAGGCCCAGAGAGGGACTCAGGTTTCTTATGGAAGGRCTT
CTCATTCATCCCTAATATAATCCTTGCAATGACCCCAAGACCTTGAGCCA
GAGGGAAGTAATGCTTCTTTGTGAGCCTCAAAAGGAGGGAAATGGCCNAG
GNTTACAGTAATATAATGACACTAATATTATTATTAATAATGGCTAATGT
```

-continued

```
GTCTCAAACGCTTCTTACGTGCTAGGCGCTGTGCCAAGTGCTTTATTTAT
ATGCATT
```

RT-PCR Exons 1-4

This sequence was created from RT-PCR to compare the ORF of affected and non-affected animals (562 bp):

SEQ ID NO: 14

```
CCAGTGGCAGCAGGAACCTCAGGATGGGCAGCAGTGGCTTGTGAGAGCCG
GCAGGGCCATTTTGGCCTTTCTCCTGCAGACTCTGTCCGGGAGGGGATGG
GGCAGCTGAGCCATGTRCACCACCCTCTTCCTACTCAGCACCTTGGCCAT
GCTCTGGCGCCGCCGGTTCGCCAACCGGGTCCAACCGGAGCCCAGCGGAG
CAGACGGGGCAGTCGTGGGCAGCAGGTCGGAGAGAGACCTCCAGTCCTCG
GGCAGAAAGGAAGAGCCTCTGAAGTAAGTCTTCACCCGGTCAGGCGGAGC
TCGGCCCCAGGGACTGGGATCAGCTGGCAGAGGCAGTTCAAGTCCCGGCT
GGCCTCTTACCCACAAAGCATGCTGTGGTGGAAGCAGCAGCAGCAGCAAG
AAGAAAAATGGGAAAAAGCAGTCATCAAGAAGGTAGACTCCTCCCTTTGA
GTCCCTGGACCTGCCTGGCCTCCCTTTGCCCCAGACCCTGGTGGTGGGGC
TCCTGAAGCAAGGCCTGGCTGGGGCAGGCTGGAGGGCAAAGACGCTCATT
GCCCTGGCTTGG.
```

The F04 mutation is bolded and presented as a G in normal and an A in prcd affected dogs.

Splice Variants

In addition to alternative splicing observed in some of the sequences obtained throughout the cloning process of the F04 gene (described above), different splice variants were identified using RT-PCR with primers located in exons 2 and 3, and with primers located in downstream predicted exons (see below).

Clone 1:

RT-PCR was performed using a primer from exon 3 (CAGTCGTGGGCAGCAGGTCGG—SEQ ID NO:15) and one from exon 8 (AATGCATATAAATAAAGCACTTGGC—SEQ ID NO:16) producing a 316 bp product:

SEQ ID NO: 17

```
CAGTCGTGGGCAGCAGGTCGGAGAGAGACCTCCAGTCCTCGGGCAGAAAG
GAAGAGCCTCTGAAGTAAGTCTTCACCCGGTCAGGCGGAGCTCGGCCCCA
GGGGTGCCCGGGGACCTTTATAGAACCTCAGTCGGGAAGAAGCCCAAGAC
CTTGAGCCAGAGGGAAGTAATGCTTCTTTGTGAGCCTCAAAAGGAGGGAA
ATGGCCAAGGTTTACAGTAATATAATGACACTAATATTATTATTAATAAT
GGCTAATGTGTCTCAAACGCTTCTTACGTGCTAGGCGCTGTGCCAAGTGC
TTTATTTATATGCATT.
```

Primers from exon 2 (GCAGCAGGTCGGAGAGAGAC—SEQ ID NO:18) and exon 5 (CTTCCCTCAGATGTGGAGTCAG—SEQ ID NO:19) were used to amplify cDNA obtained from normal and affected retina. Three different products were obtained as shown below.

Product number 1:

SEQ ID NO: 20

GCCACCGGGTCCACCGGAGCCCAGCGGAGCAGACGGGGCAGTCGTGGGCA
GCAGGTCGGAGAGAGACCTCCAGTCCTCGGGCAGAAAGGAAGAGCCTCTG
AAGTAAGTCTTCACCCGGTCAGGCGGAGCTCGGCCCCAGGGACTGGGATC
AGCTGGCAGAGGCAGTTCAAGTCCCGGCTGGCCTCTTACCCACAAAGCAT
GCTGTGGTGGAAGCAGCAGCAGCAGCAAGAAGAAAAATGGGAAAAAGCAG
TCATCAAGAAGTTTCCAGGGCACTTGCCTCTCCCCGGTCCCCAGAGCTCA
CCCCGTCACCAGCCACTCTGCTGCAGTTCTCAATAAGAAATGCCAGCTGG
GATCTGTGACATGTCTGCCTGCGGCTGGAAGGAAGCATCTCTCAACCTGT
CCTCTGAGCGTGTCTGCGTGCCTGTGTGCATGCGTGCGTGTGTTCCAAAG
GGGCAGTCGCATGTGGGAAGGGAAGAAGCCTGACACTTGTTCTTGTCAAT
CTGCTGACTGCTCAGTACCACGGCGGCTCTGCCATTTCTCCCTCACAGTC
CTGCTCGACCCAGAGCAGAGATCAAAGCAGATTTCCGCTTCTGCTCCCTG
AGATCCAGGCGCAGACCTGCAGGCAGCTGCTCCCCACTGTCTGGAAGCCA
TTCATCATGCAAAGCGCCTCCCCACCAAACCCCTGCCTGCACGTGCATCG
TCCCCCCACCATCACCATCCAGCCCCCAGGGTGGGCAGGGAGGTCCCTGC
CTAGCTGCACACCCCCCAGGCCATCAAGAGGCAGGAGATGGGGAGT.

Product number 2:

SEQ ID NO: 21

GCCACCGGGTCCACCGGAGCCCAGCGGAGCAGACGGGGCAGTCGTGGGCA
GCAGGTCGGAGAGAGACCTCCAGTCCTCGGGCAGAAAGGAAGAGCCTCTG
AAGTAAGTCTTCACCCGGTCAGGCGGAGCTCGGCCCCAGGGACTGGGATC
AGCTGGCAGAGGCAGTTCAAGTCCCGGCTGGCCTCTTACCCACAAAGCAT
GCTGTGGTGGAAGCAGCAGCAGCAGCAAGAAGAAAAATGGGAAAAAGCAG
TCATCAAGAAGAGCTCACCCCGTCACCAGCCACTCTGCTGCAGTTCTCAA
TAAGAAATGCCAGCTGGGATCTGTGACATGTCTGCCTGCGGCTGGAAGGA
AGCATCTCTCAACCTGTCCTCTGAGCGTGTCTGCGTGCCTGTGTGCATGC
GTGCGTGTGTTCCAAAGGGGCAGTCGCATGTGGGAAGGGAAGAAGCCTGA
CACTTGTTCTTGTCAATCTGCTGACTGCTCAGTACCACGGCGGCTCTGCC
ATTTCTCCCTCACAGTCCTGCTCGACCCAGAGCAGAGATCAAAGCAGATT
TCCGCTTCTGCTCCCTGAGATCCAGGCGCAGACCTGCAGGCAGCTGCTCC
CCACTGTCTGGAAGCCATTCATCATGCAAAGCGCCTCCCCACCAAACCCC
TGCCTGCACGTGCATCGTCCCCCCACCATCACCATCCAGCCCCCAGGGTG
GGCAGGGAGGTCCCTGCCTAGCTGCACACCCCCCAGGCCATCAAGAGGCA
GGAGATGGGGAGT.

Product number 3:

SEQ ID NO: 22

GCCACCGGGTCCACCGGAGCCCAGCGGAGCAGACGGGGCAGTCGTGGGCA
GCAGGTCGGAGAGAGACCTCCAGTCCTCGGGCAGAAAGGAAGAGCCTCTG
AAGTAAGTCTTCACCCGGTCAGGCGGAGCTCGGCCCCAGGGACTGGGATC
AGCTGGCAGAGGCAGTTCAAGTCCCGGCTGGCCTCTTACCCACAAAGCAT
GCTGTGGTGGAAGCAGCAGCAGCAGCAAGAAGAAAAATGGGAAAAAGCAG

-continued

TCATCAAGAAGTCCTGCTCGACCCAGAGCAGAGATCAAAGCAGATTTCCG
CTTCTGCTCCCTGAGATCCAGGCGCAGACCTGCAGGCAGCTGCTCCCCAC
TGTCTGGAAGCCATTCATCATGCAAAGCGCCTCCCCACCAAACCCCTGCC
TGCACGTGCATCGTCCCCCCACCATCACCATCCAGCCCCCAGGGTGGGCA
GGGAGGTCCCTGCCTAGCTGCACACCCCCCAGGCCATCAAGAGGCAGGAG
ATGGGGAGT.

RT-PCR was done on affected and non-affected retina using the following primers:

5'-TTAATCAGTCTGCACAAGGTCG-3' SEQ ID NO: 31

5'-GGGTCATTGCAAGGATTATATTAGG-3' SEQ ID NO: 32

Two splice variants were observed:

Product number 1:

SEQ ID NO: 33

TTAATCAGTCTGCACAAGGTCGGGTTGGCTGACCCCACTAATCAGCTTGA
GCCTCCTAATCCAGTGGCAGCAGGAACCTCAGGATGGGCAGCAGTGGCTT
GTGAGAGCCGGCAGGGCCATTTTGGCCTTTCTCCTGCAGACTCTGTCCGG
GAGGGGATGGGGCAGCTGAGCCATGT*R*CACCACCCTCTTCCTACTCAGCA
CCTTGGCCATGCTCTGGCGCCGCCGGTTCGCCAACCGGGTCCAACCGTGA
GAAGCTGATGGGGCCATGGGCAGGGATGGGGAGAGAGGAGAAGCTAGGGG
GTGAGGGGTGGTGCAGGGGCTGCCTGGACCTCCTGGGAGGCTGGAGGGCG
GGGAGGATTTGCAGGGAGGTCCAGAGAGGTTTCCCATCAGAGCACGCGGG
GGCGGGGGCTCGCAGGTGCTCCGAGACTGGCTGGAGTCCCCGGTCCCCCA
GCCCAACACGGCCAGGAGAGGGGGGTTCTGGGCCCGGGCGCTGCCCACAGC
TCTTCCAGCCTCTTCCTCCCGCCCACAGGGAGCCCAGCGGAGCAGACGGG
GCAGTCGTGGGCAGCAGGTCGGAGAGAGACCTCCAGTCCTCGGGCAGAAA
GGAAGAGCCTCTGAAGTAAGTCTTCACCCGGTCAGGCGGAGCTCGGCCCC
AGGGACTGGGATCAGCTGGCAGAGGCAGTTCAAGTCCCGGCTGGCCTCTT
ACCCACAAAGCATGCTGTGGTGGAAGCAGCAGCAGCAGCAAGAAGAAAAA
TGGGAAAAAGCAGTCATCAAGAAGGTAGACTCCTCCCTTTGAGTCCCTGG
ACCTGCCTGGCCTCCCTTTGCCCCAGACCCTGGTGGTGGGGCTCCTGAAG
CAAGGCCTGGCTGGGGCAGGCTGGAGGGCAAAGACGCTCATTGCCCTGGC
TTGGGCTCCCTTCCTCTGAGATCCTGAGGATAGTCTGAGGCAGGCCCAGA
GAGGGACTCAGGTTTCTTATGGAAGGGCTTCTCATTCATCCCTAATATAA
TCCTTGCAATGACCC

Product number 2:

SEQ ID NO: 34

TTAATCAGTCTGCACAAGGTCGGGTTGGCTGACCCCACTAATCAGCTTGA
GCCTCCTAATCCAGTGGCAGCAGGAACCTCAGGATGGGCAGCAGTGGCTT
GTGAGAGCCGGCAGGGCCATTTTGGCCTTTCTCCTGCAGACTCTGTCCGG
GAGGGGATGGGGCAGCTGAGCCATGT*R*CACCACCCTCTTCCTACTCAGCA

-continued

```
CCTTGGCCATGCTCTGGCGCCGCCGGTTCGCCAACCGGGTCCAACCGGAG

CCCAGCGGAGCAGACGGGGCAGTCGTGGGCAGCAGGTCGGAGAGAGACCT

CCAGTCCTCGGGCAGAAAGGAAGAGCCTCTGAAGTAAGTCTTCACCCGGT

CAGGCGGAGCTCGGCCCCAGGGACTGGGATCAGCTGGCAGAGGCAGTTCA

AGTCCCGGCTGGCCTCTTACCCACAAAGCATGCTGTGGTGGAAGCAGCAG

CAGCAGCAAGAAGAAAAATGGGAAAAAGCAGTCATCAAGAAGGTAGACTC

CTCCCTTTGAGTCCCTGGACCTGCCTGGCCTCCCTTTGCCCCAGACCCTG

GTGGTGGGGCTCCTGAAGCAAGGCCTGGCTGGGGCAGGCTGGAGGGCAAA

GACGCTCATTGCCCTGGCTTGGGCTCCCTTCCTCTGAGATCCTGAGGATA

GTCTGAGGCAGGCCCAGAGAGGGACTCAGGTTTCTTATGGAAGGGCTTCT

TCATTCATCCCTAATATAATCCTTGCAATGACCC
```

The above results indicate that there are several retinal splice variants of F04. Based on these splice variants and comparative genomic analysis, the genomic organization of F04 was characterized. However, all splice variants relevant to prcd include exons 1-4 and the shortest and most abundantly expressed such disease-relevant transcript is the cDNA identified as SEQ ID No:3.

EXAMPLE 2

Since mapping the prcd locus to canine chromosome 9 (CFA9), we have mapped the prcd disease interval at higher resolution, narrowed the identified canine genomic region in which the prcd gene is located, and tested all candidate genes within that region. Initially, we created a physical map of the region using canine BACs (Sidjanin, 2003), and identified multiple polymorphic markers within and flanking this region. Examination of genotypes of prcd-affected dogs from multiple breeds for these polymorphic markers established that within breeds the haplotype that cosegregated with the prcd mutation extended across a broad region, including the physically mapped interval (Sidjanin et al., 2003). However, comparison of these genotypes revealed that the breed specific haplotypes varied among breeds within the area initially published (Sidjanin et al., 2003), but was consistent for all breeds for a set of markers physically located within a single BAC clone (BAC #10M13; Li et al, 1999) located adjacent to the area initially published. This BAC clone contained several genes. Single nucleotide polymorphisms were identified for each of these genes, and a single haplotype was constructed which differentiated the prcd-transmitting CFA9 from that of all normal dogs tested (Table 1) in all breeds known to be affected with prcd.

TABLE 1

Linkage disequilibrium (LD) region flanking the canine prcd/F04 gene on canine chromosome 9 (CFA9). All genes in this region are located in canine BAC# 10M13.

| Polymorphism # | Polymorphism Name | Affected allele | Alternative allele | Polymorphism Location |
|---|---|---|---|---|
| 1 | | A | G | FLJ22341 |
| 2 | p43 | G | T | FLJ22341 |
| 3 | | C | T | FLJ22341 |
| 4 | | C | T | FLJ22341 |
| 5 | b712 | A | C | FLJ22341 |
| 6 | b817 | deletion | CTG | FLJ22341 |
| 7 | b1149 | T | C | FLJ22341 |
| 8 | p49 | C | T | FLJ22341 |
| 9 | | T | G | FLJ22341 |
| 10 | SINE | no SINE | SINE | FLJ22341 |
| 11 | p48 | G | A | FLJ22341 |
| 12 | | A | G | FLJ22341 |
| 13 | | A | G | FLJ22341 |
| 14 | | T | C | FLJ22341 |
| 15 | | C | T | FLJ22341 |
| 16 | p45 | T | C | FLJ22341 |
| 17 | p41 | C | T | FLJ22341 |
| 18 | | C | T | FLJ22341 |
| 19 | b682 | C | G | FLJ22341 |
| 20 | b937 | A | G | FLJ22341 |
| 21 | b1130 | A | G | FLJ22341 |
| 22 | b1275 | G | deletion | FLJ22341 |
| 23 | b1351 | G | A | FLJ22341 |
| 24 | p38 | T | C | CYGB |
| 25 | | G | A | CYGB |
| 26 | | A | G | CYGB |
| 27 | CYGB | T | C | CYGB |
| 28 | b3128 | T | C | CYGB |
| 29 | b3133 | T | C | CYGB |
| 30 | b3605 | C | G | CYGB |
| 31 | b3769 | C | G | CYGB |
| 32 | 3820-23 | deletion | TGCC | CYGB |
| 33 | p40 | A | G | CYGB |
| 34 | | G | A | CYGB |

TABLE 1-continued

Linkage disequilibrium (LD) region flanking the canine prcd/F04 gene on canine chromosome 9 (CFA9). All genes in this region are located in canine BAC# 10M13.

| Polymorphism # | Polymorphism Name | Affected allele | Alternative allele | Polymorphism Location |
|---|---|---|---|---|
| 35 | | A | G | CYGB |
| 36 | 31F5 | A | C | CYGB |
| 37 | 31F4 | A | G | CYGB |
| 38 | | A | G | |
| 39 | **285** | **C** | **T** | F04 |
| 40 | **851** | **C** | **G** | F04 |
| 41 | **999** | **C** | **T** | F04 |
| 42 | **1298** | **A** | **G** | F04 |
| 43 | **1633-1635** | **CTT** | **deletion** | F04 |
| 44 | **1854** | **deletion** | **C** | F04 |
| 45 | **1912** | **C** | **G** | F04 |
| 46 | **2413** | **A** | **G** | F04 |
| 47 | **2590** | **T** | **C** | F04 |
| 48 | **2601-2603** | **deletion** | **TCC** | F04 |
| 49 | **2607** | **A** | **G** | F04 |
| 50 | **2660-2666** | **ATGAGAA** | **deletion** | F04 |
| 51 | **2710** | **C** | **T** | F04 |
| 52 | **2741** | **G** | **A** | F04 |
| 53 | **2769** | **C** | **T** | F04 |
| 54 | **3119** | **G** | **A** | F04 |
| 55 | **3804** | **C** | **T** | F04 |
| 56 | **3971** | **G** | **C** | F04 |
| 57 | **4459** | **G** | **A** | F04 |
| 58 | **5244** | **G** | **A** | F04 |
| 59 | **5698** | **G** | **T** | F04 |
| 60 | **6254** | **A** | **C** | F04 |
| 61 | **6318** | **deletion** | **G** | F04 |
| 62 | **6953** | **T** | **C** | F04 |
| 63 | **7030** | **T** | **A** | F04 |
| 64 | **7183** | **A** | **C** | F04 |
| 65 | **7239** | **G** | **A** | F04 |
| 66 | **7855** | **A** | **G** | F04 |
| 67 | **8230** | **C** | **T** | F04 |
| 68 | **8843** | **G** | **deletion** | F04 |
| 69 | **8977** | **G** | **A** | F04 |
| 70 | **10230** | **A** | **G** | F04 |
| 71 | **10268** | **A** | **C** | F04 |
| 72 | **10855** | **A** | **T** | F04 |
| 73 | **12175** | **A** | **G** | F04 |
| 74 | **12613** | **A** | **G** | F04 |
| 75 | **15033** | **C** | **T** | F04 |
| 76 | **15347** | **G** | **A** | F04 |
| 77 | **15359** | **A** | **T** | F04 |
| 78 | **15445** | **T** | **C** | F04 |
| 79 | **17200** | **T** | **C** | F04 |
| 80 | **17407** | **deletion** | **C** | F04 |
| 81 | **17435-17437** | **GGG** | **deletion** | F04 |
| 82 | **17672** | **T** | **deletion** | F04 |
| 83 | **17892** | **A** | **G** | F04 |
| 84 | b1409 | C | T | STHM |
| 85 | p2 | A | C | STHM |
| 86 | STHM-NaeI | A | G | STHM |
| 87 | STHM- AvaI | C | T | STHM |
| 88 | base 3526 | C | T | STHM |
| 89 | base 3655 | G | A | STHM |
| 90 | 10-299 | G | A | STHM |
| 91 | 10-597 | G | G | STHM |
| 92 | b2263 | deletion | T | STHM |
| 93 | b2411 | T | C | STHM |
| 94 | b2425 | deletion | C | STHM |
| 95 | b2748 | G | deletion | STHM |
| 96 | from RT-PCR | A | G | STHM |

The "affected allele" for each polymorphism is that found on all examined prcd-transmitting chromosomes from dogs of multiple breeds; the "alternative allele" is that which is present, for example, in BAC # 10M13. Where polymorphism information is bolded, the Polymorphism Name indicates the position (base number) in the F04 genomic sequence (i.e. SEQ ID NO: 1). Polymorphism Location indicates the gene in the genomic sequence of which the polymorphism is located.

For each of these genes the exons were sequenced and examined, and a disease associated sequence change (i.e. a mutation) was found in only one gene. This gene, referred to herein as F04, is located within the interval described in U.S. Pat. No. 5,804,388. Details of the canine cDNA and genomic DNA sequence for F04 have been provided above. The mutation, at nucleotide 1298 of SEQ ID NO: 1 represents a G to A transition, from normal sequence to affected. We refer to this sequence change as the "prcd mutation" in F04 gene herein and is shown as polymorphism no. 42 in the table above.

EXAMPLE 3

This example describes a PCR-based restriction enzyme digestion test developed to identify the sequence change in the F04 gene. The following primers were used:

primer 1: ccagtggcagcaggaacc—SEQ ID NO:27 primer 2: ccgacctgctgcccacgactg—SEQ ID NO:28

PCR is run under standard conditions (annealing temp 58 degree C., 1.5MgCl2) in 25 microliters, 35 cycles. The amplification product is 512 bp in size (corresponding to bp 1182 to 1693 in SEQ ID NO:1. The restriction enzyme RsaI digests the amplification product bearing the A allele, but not the G allele. Conversely, ApaLI digests the G allele but not the A allele. Both digests were performed at 37° C. for 2 hours.

Restriction digestion thus yields the diagnostic results shown in Table 2:

TABLE 2

| ENZYME (restriction site) | ALLELE | FRAGMENT SIZE(S) (bp) |
|---|---|---|
| RsaI (GT|AC) | G | 512 |
| | A | 116; 396 |
| ApaLI (G|TGCAC) | G | 115; 397 |
| | A | 512 |

A large population of dogs affected with prcd was examined. We have tested more than 100 affected animals from 13 different breeds or breed varieties. These include: 36 Australian cattle dogs, 2 Chinese crested, 5 English cocker spaniels, 5 Finish Laphunds, 48 Labrador retrievers, 45 miniature or toy poodles, 1 Nova Scotia duck tolling retriever, 3 Portuguese water dogs, 1 Silky Terrier, 25 American eskimos, and 14 Entlebucher mountain dogs.

An example of the identification of the G allele (normal) and the A allele (affected allele) following RsaI digestion is shown in FIG. 3A and following digestion with ApaLI is shown in FIG. 3B. For the RsaI digestion (FIG. 3A), a normal dog (GG) shows a product of 512 bp, an affected dog (AA) shows products of 396 bp and 116 bp while a carrier dog (AG) shows products of 512 bp, 396 p and 116 bp. For the ApaLI digestion (FIG. 3B), a normal dog (GG) shows products of 397 bp and 115 bp, an affected dog (AA) shows a product of 512 bp, and a carrier dog (AG) shows products of 512 bp, 397 bp and 115 bp. Thus, this method can be used for identification of normal dogs (i.e., in which both alleles of the F04 gene have G as the nucleotide at a position corresponding to nucleotide position 1298 of SEQ ID NO:1), carrier dogs (i.e., in which one allele has G and the other allele has A as the nucleotide at a position corresponding to nucleotide position 1298 of SEQ ID NO:1) and affected or predisposed dogs (i.e., dogs in which both alleles of the F04 gene have A as the nucleotide as a position corresponding to nucleotide position 1298 of SEQ ID NO:1).

EXAMPLE 4

To confirm the exclusion of the affected allele from the general dog population, we tested 1,000 animals from 67 breeds not known to have the prcd form of PRA, to establish the absence of the "A" allele. These dogs were tested by Pyrosequencing (Biotage, Charlottesville, Va.; <http://www.pyrosequencing.com/DynPage.aspx>, Fakhrai-Rad et al., 2002; Ronagi et al., 2002; Shendure et al., May 2004) as follows. The technique is based on the amplification of the target sequence with an unlabeled forward primer and a biotin labeled (5'Bio) reverse primer, which are used to isolate a single stranded DNA product. A sequencing primer is used to start a subsequent nucleotide specific primer extension and presence or absence of a nucleotide is recorded in an allele frequency dependent manner based on a luciferase reaction.

```
                                        SEQ ID NO: 23
Forward primer:     5'TTGTGAGAGCCGGCAGG3'

                                        SEQ ID NO: 24
Reverse primer:     5'Bio/ATGGCCAAGGTGCTGAGTAG3'

                                        SEQ ID NO: 25
Sequencing primer:  5'GGGGCAGCTGAGCCA3'
```

Figure 4:
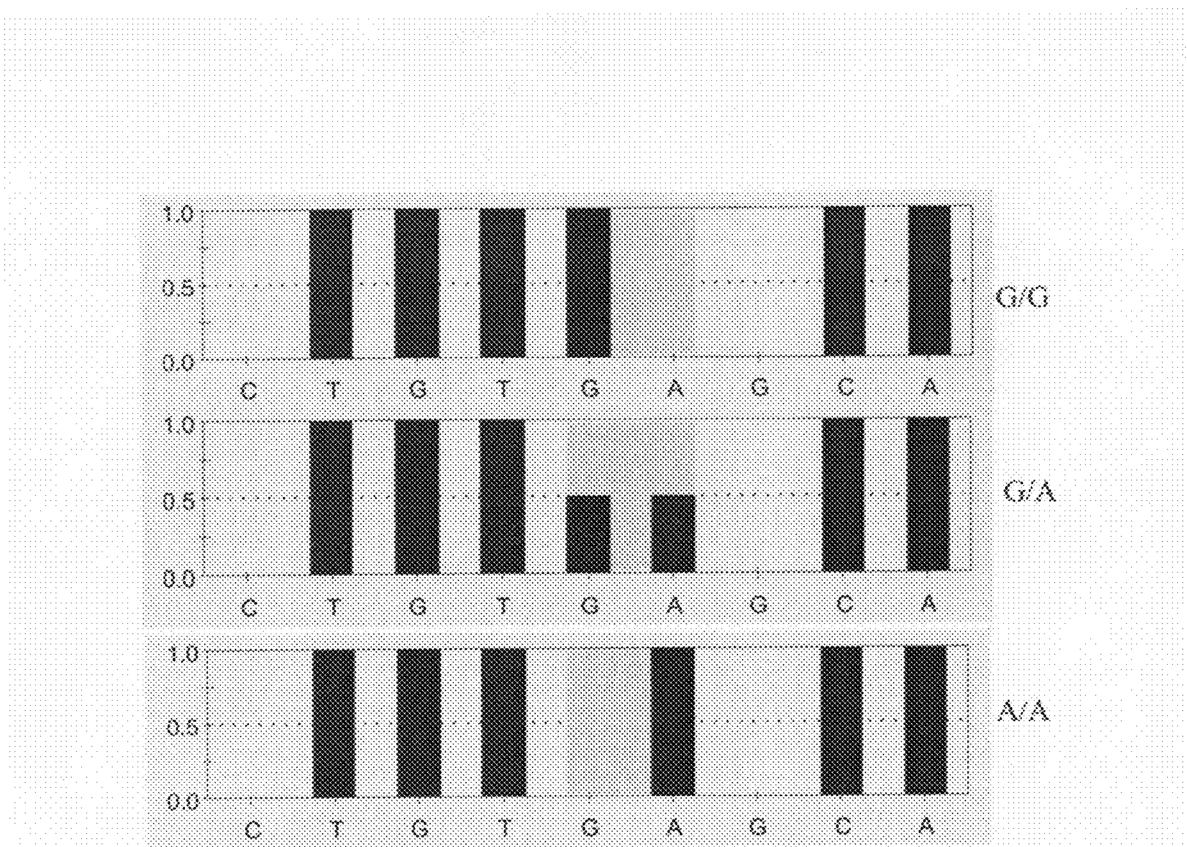
FIG. 4 is an illustration of the experimental setup used to identify whether a dog is a carrier, is affected with or is normal with respect to the prcd mutation, using Pyrosequencing™.

Product: 113 bp (primer sequence is shown in capital letter, the G/A polymorphism is bolded, and Bio indicates the biotin label: TTGTGAGAGCCGGCAGGggccattttggcctttctcctgcagactctgtccgggaggggatGGGGCA GCTGAGCCAtgtg/acaccaccctcttcCTACTCAGCACCTTGGCCAT—Bio—SEQ ID NO:26 FIG. 4 illustrates the test set-up for the procedures of this example. Based on the test sequence, a series of nucleotides is injected one at the time during the primer extension (the sequence is shown on the bottom of each panel) and the resulting light reaction is registered (indicated by the bar for each nucleotide, directly proportional to the amount of alleles present). Nucleotides one (C) and 7 (G) of the sequence are negative controls and should not produce any light reaction. Positions 2, 3, 4, 8 and 9 are positive controls and react the same in all samples based on the tested sequence. The mutation in question corresponds to nucleotides 5 and 6. In normal animals, only the G allele is present and produces a reaction of the same strength as the positive controls. In affected individuals the same is true for the A allele, while carriers have both alleles at a 50/50 ratio and, therefore, produce half the intensity at each position. In all cases, the animals tested by Pyrosequencing™ were "GG", i.e., they had G in both alleles of the F04 gene at a position corresponding to position 1298 of SEQ ID NO:1.

It will be appreciated by those skilled in the art that routine modifications can be made to the various embodiments described above. Such modifications are intended to be within the scope of the present invention.

REFERENCES

1. Aguirre, G. D.: Inherited Retinal Degenerations in the Dog Trans. Amer. Acad. Ophth. and Otol. 81: 667, 1976.
2. Aguirre G D, Acland G M. Variation in Retinal Degeneration Phenotype Inherited at the prcd Locus. Exp. Eye Res. 46: 663, 1988
3. Acland G, Fletcher R T, Gentleman S, Chader, G. and Aguirre, G: Non-allelism of Three Genes (rcd1, rcd2 and erd) for Early-Onset Hereditary Retinal Degeneration. Exp. Eye Res. 49: 983, 1989.

4 Aguirre, G. and Acland, G.: Inherited Retinal Degeneration in the Labrador Retriever Dog. A New Animal Model of RP? Invest. Ophthalmol. Vis Sci. (Supp). 32(4), 1991;

5. Acland, G., Ray, K., Mellersh, C., Gu, W., Langston, A., Rine, J., Ostrander, E., and Aguirre, G. Linkage analysis and comparative mapping of canine progressive rod-cone degeneration (prcd) establishes potential locus homology with retinitis pigmentosa (RP17) in humans. Proc. Natl. Acad. Sci. USA. 95:3048-3053, 1998.

6. Fakhrai-Rad, H., Pourmand, N., Ronaghi, M. Pyrosequencing: An accurate detection platform for single nucleotide polymorphisms. Human Mutation, 2002; 19(5).

7. Kijas, J. W., Cideciyan, A. V., Aleman, T. S., Pianta, M. J., Pearce-Kelling, S. E., Miller, B. J., Jacobson, S, G., Aguirre, G. D., and Acland, G. M. Naturally-occurring rhodopsin mutation in the dog causes retinal dysfunction and degeneration mimicking human dominant retinitis pigmentosa Proc. Natl. Acad. Sciences USA 99:6328-6333, 2002.

8. Li, R., Mignot, E., Faraco, J., Kadotani, H., Cantanese, J., Zhao, B., Lin, X., Hinton, L., Ostrander, E. A., Patterson, D. F., et al. 1999. Construction and characterization of an eightfold redundant dog genomic bacterial artificial chromosome library. Genomics 58: 9-17.

9. Pearce-Kelling, S. E., Nickle, A., Kijas, J. W., Sidjanin, D. J., Miller, B. J., Aguirre, G. D. and Acland, G. M. 2002.

10. Ronagi M, Elahi E. Discovery of Single Nucleotide Polymorphisms and mutations by Pyrosequencing. Comp Funct Gemon. 2002; 3: 51-56.

11. Shendure J, Mitra R D, Varma C, Church G M. Advanced sequencing technologies: methods and goals. Nature Reviews Genetics, May 2004; 5(5), 335-344.

12. Sidjanin, D. J., Miller, B., Kijas, J. K., McElwee, J., Pillardy, J., Malek, J., Pai, G., Feldblyum, T., Fraser, C., Acland, G. and Aguirre, G. Radiation Hybrid Map, Physical Map and Low-Pass Genomic Sequence of the Canine prcd Region on CFA9, and Comparative Mapping with the Syntenic Region on Human Chromosome 17. Genomics 81:138-148, 2003.

13. Zhang, Q., Acland, G. M., Wu, W. X., Johnson, J. L. Pearce-Kelling, S., Tulloch, B., Vervoort, R., Wright, A. F., Aguirre, G. D. Different RPGR exon ORF15 Mutations in Canids Provide Insights into Photoreceptor Cell Degeneration Hum. Molec. Genet. 11:993-1003, 2002.

The invention claimed is:

1. An isolated polynucleotide comprising a DNA sequence of SEQ ID NO:1, a RNA sequence corresponding to SEQ ID NO:1, the DNA sequence complementary to SEQ ID NO:1 or the RNA sequence complementary to SEQ ID NO:1.

2. An isolated polynucleotide comprising a DNA sequence of SEQ ID NO:3, a RNA sequence corresponding to SEQ ID NO:3, the DNA sequence complementary to SEQ ID NO:3 or the RNA sequence complementary to SEQ ID NO:3.

* * * * *

SEQUENCE LISTING

```
<160> NUMBER OF SEQ ID NOS: 34

<210> SEQ ID NO 1
<211> LENGTH: 18592
<212> TYPE: DNA
<213> ORGANISM: canis familiaris

<400> SEQUENCE: 1

cggccaggtg gcacctctga ctcccagccc aaacctgatg ccagtgtcca        50

cttctccctg tcgctccctc gcgaccccgc ccttctcaag acttggtgtc       100

cctctgcaag tgtgagaaga ggtcggctca cctcttccgc tttggcttat       150

gtattttaaa aatcgttttt caaagtagag agcccaggtg cagccccagc       200

tctggccctc cctgggagcc tgggcaggag acccccttgac accgcttcca       250

tctccttgga gggaaggaaa atctagtgca gaccyctggg gtttttggag       300

agggctggag gaagctggat gctcagaccc ctgtgtgctc cacatgctgc       350

ctgggccacc tcactgaacc cctctgacag gacacccgat gcctgtgcgg       400

tgcccttcca agtggctgct cagaagcttt gcactgggaa agcaagtatt       450

cgctatttct atttagtatt tctatttagc tttatctcat cttttacaag       500

tcttatgtgt gtttattatg caggactgta ttcgcacaga tgtggaagat       550

ctaatgtatg agcagatgca tatacttatt tcatgagtgc acacttaaat       600

ccagtctttt atggaagggg ctatggaaat cagtaacatt tggggaggac       650

tgtccagagg ggagaacaca actgctcagc cgcccctcca ctccccggcc       700

tcccttgtct ttctggcttc attatctaat attcttcctc ccctccccat       750

ggctctccat gacatcattg ttctgccaac actcaacttc cagttgctgg       800

aacatgctct gtgcttttgt gtcagccgcc ccggaagagt cttctgttgg       850

sggggaggta accttccttg aacacctgca aattccaatg cccccagctc       900

ctctcccaag cattccctga cacatgcaac tccgaaagtg ctctgcgggt       950
```

-continued

```
gcctctcatc acccaagtcg ctctactgtg gtcattaatg tgacttgcya      1000
gctcaagtgt ctagactaga agccccttga gggttaggcc caggtcctag      1050
tcacatctgt atccagaatg gacagcttga tttaccctgc caccgcaggc      1100
gacaacttgg gcccagtgag gttaatcagt ctgcacaagg tcgggttggc      1150
tgaccccact aatcagcttg agcctcctaa tccagtggca gcaggaacct      1200
caggatgggc agcagtggct tgtgagagcc ggcagggcca ttttggcctt      1250
tctcctgcag actctgtccg ggaggggatg gggcagctga gccatgtrca      1300
ccaccctctt cctactcagc accttggcca tgctctggcg ccgccggttc      1350
gccaaccggg tccaaccgtg agaagctgat ggggccatgg gcagggatgg      1400
ggagagagga gaagctaggg ggtgaggggt ggtgcagggg ctgcctggac      1450
ctcctgggag gctggagggc ggggaggatt tgcagggagg tccagagagg      1500
tttcccatca gagcacgcgg gggcgggggc tcgcaggtgc tccgagactg      1550
gctggagtcc ccggtccccc agcccaacac ggccaggaga gggggttctg      1600
ggcccgggcg ctgcccacag ctcttccagc ctcttcctcc cgcccacagg      1650
gagcccagcg gagcagacgg ggcagtcgtg ggcagcaggt cggagagaga      1700
cctccagtcc tcgggcaggt aaggcagagt ctgggctggg ggaggcaggg      1750
tgcgtcgagg aagcggctgc cctggccgcc ccgaccgtgc ctgggcaggt      1800
acatgagtgc acccgagccg gcgcgccggg gcccctcgcc ccagccaccc      1850
ggtccccgtg tgcccggtgg gcagcctcgg tgtctgtgct cccccgcggc      1900
actgggcgcc csggcctgtc ctctgcaccg cagctgctct gctttgcccg      1950
agtgcggggt ggtcccccgg gtcccatcgg aaggcgcggg gggaccggag      2000
aggatggggc aggagcagct ccgggcggcc ggctcgctgc ccttcccccct     2050
ccccgcggcc cccgctccgc ctcagccgct cccctgcccc ggccgccggc      2100
gggattcgcc caccggcccc caataggagg cgcaggagcg gcatgacgtc      2150
atcggcaccg cctgccattg gctgggcagc tcctgcgggc aggtcgctgt      2200
ctccagcggc cgaaagttaa ctcttcccta ggccgaagcc atgtggctcc      2250
acaagggggg aagtttgggg aacttctgga ttcttccttc cctgggtgac      2300
cagtgtcctt tgatgttagg ggctcctatg cccaacaaac cacggaaaaa      2350
tcaacatgca tttattaaga acataccgtt gtgcgtgttc ttttgtgccc      2400
ccggacccac ctrgtggggg agtcctgtgt gaagggacat tctctcctgc      2450
aaaaggtcta ctagccttct ctcaactcta gtgagacaaa gcacatgatg      2500
cccttgggct ccggggcctg tggctggagg gagtctcccc acagcgctca      2550
gatggctgag ccagtgagcg tgcctgcctg ctggggcacy ccaccggctc      2600
tcctccrggt gtgtaggacc tgcctgggtg cccctcagcc atgtggagac      2650
tggcgagcca tgagaaatga gaatgggaat ctgtctccgt atgcggcccc      2700
aaattcctcy tcggtgctgg gattcctcca agctctgaat rtcaggaggg      2750
cagccctggg catgtgccyg agacaggtat ttctgggcca cccttccttg      2800
acaatctagg ctagctgaga tggtcatgat actacccaag taggcctgct      2850
ggtgaaatgg gctgacaaag gtgaaatgat gagcactggg cctcacgcag      2900
agcaggccct tgaatgacta gtcctccctg ttgagtttgg gtctggaggc      2950
```

-continued

```
ggacagccag agtccacatc ctgactccct gcttcctgac cgagagcctc        3000
tgggaaagct atgtgatctt tctatttgta tataaactgg gattaataac        3050
agaatggtgt gggggtgttt gtgaggttca aattgagatc atcctaaagc        3100
acttggcacg aaacagctrt ttaataaatg ccggctagct attctcctgt        3150
tgttacctgg ctcttgatca gtgttctatt cttcccttga ggtctcttaa        3200
acgttaactc acttggaagt tgtaacagcc ccagagggtt ggcaagacaa        3250
gtgtttctat ctcttgttaa tggtggagga aactgaggga aggggaggcg        3300
tcagtttttc actcgaggtc atccatccta tttgtggctg atggcaactg        3350
acttcaggta gtcggtctcc tctacatgaa atgggcctgg accctccctg        3400
tcaggagaaa aaagctgaat ctggaccatc tggcccagcc tcgtggggtc        3450
tagccagaag gaagcagttg cctgttaact cccagggacc cagttaactg        3500
gaaaaatcag cctaacatcc aacacctcct gcttcgggtg gctgttgtga        3550
agggctggtc tggggagcag taggcatgac atttctgctc tgcaattcca        3600
cagtcacaaa ttccagctga tttcctggct gctcctaccc ctcagtagtg        3650
gggtgcctcc ctaggcgtgg ggcaaaggga agaagtctgg aaagacggga        3700
aggacgtccc cttcaatcct ctgactccca tgcttttctg tttagaaagg        3750
aagagcctct gaagtaagtc ttcacccggt caggcggagc tcggccccag        3800
ggaytgggat cagctggcag aggcaggtag ggcagggctg caagccttgg        3850
aaggtagagg gctgggctgg ggacaaggca ggctctgcaa ggcctggcca        3900
tgagggagca gagctccatg gagggtacac agaaggcggg tggcctctca        3950
tcagctcctg cctcaagcct sctgtggtcc aggccatggc gcaaggcttt        4000
gttagtttta agggaagggc gtgtggtgaa gtggtggtca tgctggcact        4050
gtagtgccag aggacttcta agggagaggg tgtgctctgg aatatccatt        4100
ctgcaatgca agcccctgcc ttgggatggg aggaagtgcc aatctggttt        4150
tctatttcag ttcaagtccc ggctggcctc ttacccacaa agcatgctgt        4200
ggtggaagca gcagcagcag caagaagaaa aatgggaaaa agcagtcatc        4250
aagaaggtag actcctccct ttgagtccct ggacctgcct ggcctccctt        4300
tgccccagac cctggtggtg gggctcctga agcaaggcct ggctggggca        4350
ggctggaggg caaagacgct cattgccctg gcttgggctc ccttcctctg        4400
agatcctgag gatagtctga ggcaggccca gagagggact caggtttctt        4450
atggaaggrc ttctcattca tccctaatat aatccttgca atgacccaag        4500
aagactgggc gtgttattat ccacactttt ggaaatgagg aaacagagag        4550
aggttaagga atctgtccag tgtcatccag ctagttaatc ctgcccccca        4600
cccccaccca ccccccgccc tcccagcctc ctttggaggc tgcagagccc        4650
acactcttac ccaccagggc acaggcctct ctgaaatcac ctggaagttt        4700
gcagcttgca gctgctatgt gagagcaggg gttccacggg cccggcagcc        4750
ccaaagcctg tggtccaagg ctgtgtggta tcagtttgcc atggtggcgc        4800
tctagtttcc agggcacttg cctctccccg gtccccagag ctcaccccgt        4850
caccagccac tctgctgcag ttctcaataa gaaatgccag ctgggatctg        4900
```

-continued

```
tgacatgtct gcctgcggct ggaaggaagc atctctcaac ctgtcctctg          4950
agcgtgtctg cgtgcctgtg tgcatgcgtg cgtgtgttcc aaaggggcag          5000
tcgcatgtgg gaagggaaga agcctgacac ttgttcttgt caatctgctg          5050
actgctcagt accacggcgg ctctgccatt tctccctcac agtcctgctc          5100
gacccagagc agagatcaaa gcagatttcc gcttctgctc cctgagatcc          5150
aggcgcagac ctgcaggcag ctgctcccca ctgtctggaa gccattcatc          5200
atgcaaagcg cctccccacc aaacccctgc ctgcacgtgc atcrtccccc          5250
caccatcacc atccagcccc cagggtgggc agggaggtcc ctgcctagct          5300
gcacaccccc caggccatca agaggcagga gatggggagt tctctcgaca          5350
gcagcctgtc tgccgccctg actccacatc tgagggaagg aaggaaaggg          5400
tgagatgcca cagacagagg ggaccacgct gaagccatgg gggaggggct          5450
gctgatcttg ccctggaagc ctctagaagt agggcagggt ggaggcaggg          5500
gaagggtcaa accaggggaa ggagctgtgc gctggaatgg cgacagagcc          5550
ccaccgccca ctcgacatgg gccaggagtt cgtgaccacc tgtctcagct          5600
cctgtcagcc tgtctttctc ctgcgaggtg ttggccttcc ttggtgacag          5650
ggctgtcggg ctgagggcca ggggcaccgt tcctggggcc cccatctkcg          5700
tccccgagcc cacctgtgta ttcatcctct aatctgtttg ccatgctcct          5750
gtcacttcag cctcggctct gctctctacc atttccacgt tgcctgcctc          5800
cttgcactag tctgaggaat tgtcaggcca aggtcacctg gctggacagg          5850
ggctggccca cggcccagac acacctccac gaggcgacac cccttcgctg          5900
cactgttcta gggacctgct caggagaggg tggctcctct gggcctcggt          5950
cccagaggga aggagagaag gggaagggaa gggctgctgg cgatgggggg          6000
actgtgtcgg ctggccttgg cggttgcccg ggccctggca gctggggtgc          6050
catgtgggct gggcgggagg ggccctctcc cccagggagc aggctggctt          6100
cggtgggagc agattgtgtt tacaccttcc ccacacaccc agcccacgct          6150
cgcctcttat tccccgggac tctcccaccc ctgggctctc tctgcaccac          6200
gggcacgttt gcagctcctc tcctgctgca ggaagttgcc gccctcagca          6250
gagmgctcct ctacagaagg ctgccagggc ccaggcgctc cctcctcggc          6300
ccactatctc ccgtcgtggg gggggaccca gtgtccccaa gaggctgaat          6350
ccacccaccc cccatttcct tggaaaacag ctgctgcttg ggaatggggg          6400
caggaaggaa agcccggggg gcttggcaga cttgaccata ataggaggga          6450
agggattaag ggcaaccaga gagagagggc cgagagagcc ggggcgcctc          6500
tggcctcagg gtgcatgaga taatgtagaa tttaagctcg gggagtccag          6550
ctccaagctc tggatttgaa tcttgactcc accatcactt tccagttctg          6600
tggcctcggg tgggttactg aatgtaaacc tgtctcagag ttgtaagggt          6650
taaattagat aatgggtata aagtgcttcg cgcacttagt aagcacgcag          6700
tatatctgag cccagggtgg ggggacagtg tttgtgagct gtcagccact          6750
gaacaactgg tcactttgca acaaccgtag gttcagaaca gctagtcctt          6800
tacctcctca ccccatggcc cttcctgccc tgtctttcca catacacaac          6850
agcagggtga tgggcagttc tggaacaaac cagagcccag cacaggggca          6900
```

-continued

```
cctggtagga cccagcaccc gggaaggctg gacgatggag caccacggtt    6950
gcytctgggt gcctggaacc ctgtccccac ctccagtggg agtcctgacc    7000
tggacatctt ccctccaact ggctctgcgw ccccaaatga atctcagctc    7050
ctagagaaga caggaggcca tggccctggt gcctttatgg tcctctgtct    7100
gaatgctaat ctctttactg gctggagcct gagtgacagg gaaaaggcgg    7150
ttctgagctg cagggtggcc gagggcggca ggmgggagca gggaggtgct    7200
gttgtctgct acttctgtgg ctgctgccag tctctcctrg agatgggaac    7250
atgaccagag agctaatgag gtggcggggg tgggggtggg ggagaaaggg    7300
aggcagacgg agcagctgca gcagctgcca ctgccctgtg tcaccccagg    7350
gtgcaaatgc caccacgggg agcaccccgc ccatcccgaa ctgtgtggct    7400
gtgcagatgc gggcaggatg gtcctgggca caggccttgg tccaagacca    7450
ggcaggcgtg gtacttgatc tgaggtgggc atcatggcac aggagctggt    7500
cccaggggtg cccggggacc tttatagaac ctcagtcggg aagaagccca    7550
agaccttgag ccagagggaa gtaatgcttc tttgtgagcc tcaaaaggag    7600
ggaaatggcc aaggtttaca gtaatataat gacactaata ttattattaa    7650
taatggctaa tgtgtctcaa acgcttctta cgtgctaggc gctgtgccaa    7700
gtgctttatt tatatgcatt gtctcattta tggggcagga actgttgtca    7750
gtctcattta cccaataagg aaagtgcttg ctcaaggtca cccacagtga    7800
gtagtgaagc caggacgtgt tccccggcaa ggtgatgtaa aagcctgtga    7850
aggtrttggg cctcgaggac atcctgggag tgtgacctgt ccaccagggc    7900
acagggcatg agagctggca accctccctg gtgatactgc cgctgctcag    7950
tctgcagaaa ctcatcattc caggctggac cagactctgg gccccgaggg    8000
cagtgaccag agccaccttt ccaggatctg tcatgctcct cagggaggaa    8050
gcagtggcca ctggcaggga tgacagatat caaggttgtc actcattgct    8100
gctgttgctc tgctgtttcc tccaaccagg ggcagagccc tgggggtaag    8150
ggagggtggc agccagcagc ccagccagag aaggaggagc cagaggagga    8200
aggctttgtt gtttgttttt acagggggay ggtgcagggc tttaaggagg    8250
tggcttcaag acctgctgac tttagccata aactggtacc taagggtgct    8300
ggaccctctc tgtgggatac atatgccccc tagtggggat taagcctgga    8350
gggtggctga gaaaattaaa gcaaaacaaa acaaaaaaag atttactgat    8400
aggctatatg acctccgaac ctggatagga agggccaggg ctggccccct    8450
gtgtccccga gattgcacaa gcacgcacag gtttaagaca atttgcagaa    8500
cccaggtgaa cgaagcattg aaagaaatta tttaatttat tccttggtca    8550
tttatttaag aagcatgtat cgggagcctg tgatgtacac accctgtggt    8600
aggtgttgga gtcagacagc aatcaaaggg acggcgcccg atgtgccaat    8650
gaggacgaca gaaagatcct ggccgaggag gccagttgtg caagctcagc    8700
cgctgcctgc cacgactttt acttctctgg acctcagtct ccccatgtaa    8750
taggcagtgt tgaacctaag tgggctggtg cagaggatgg gaaggaccac    8800
tgactaccct ggtaaaatga aggggatgga cttcttgacc tcgggggggg    8850
```

-continued

```
ccccttccaga ttcaagacag gctacagtgg acagtgtttg gaggtgctga        8900
caacggtgac tcgcccactc agcaagcgtg tatggagctc ctgtatgcca         8950
ggcattgtgg gtggcagaaa tgaagcrccc agaaaactgg acaaaactga         9000
agaagcaaca gacacttgac tacaaggaac atccaagatg gtgatcccgt         9050
gaccacctca gcatctacct cccacaggtc cctgcctgag cacagggagg         9100
ggaaacccag aggactgcag tggtcttgtt cagctgagga gacaagatca         9150
gagctcagaa cagtgtgctg ttcctaaaga tatacacaca catcaatggc         9200
atctccaaaa cagacacaac gaagatgatc caatggagaa agaaaagccc         9250
ttttgaggaa acacaaaaag tgctaaccat aaaagaaaaa aacagataaa         9300
ttggacttga tcaaaattct tggaaagact ggaagagaat actagccaag         9350
caaaaatccg aacaagggcc tgtatccaaa atatataaag aacttttaca         9400
actcaataag aagacgacag cccaacggaa aagtggggga gggttttaat         9450
agacacttcg caagaaacta gacatatggc caataaacac ataaaaagat         9500
acacaacatc ctaagccatc aaggaaatgc aaattaaaac cacaatgaga         9550
tactactgca cactcaccag aatggataaa agatggacca taatagacgt         9600
gggtgaaggt gtggagcaac ttgtaaccct gtcatacgtt gctgggaaac         9650
ctgtttggca gtttcttagg atgtaatcca agaggagtga acatgtaggt         9700
ccacacaaag atttgtacag agatgttcac agcagtgtta ttatcaataa         9750
ttagtatcca aactggaaac aacgcagata gccatcaaga ggtaaatgga         9800
taaaaaaaaa aaaaaaaaaa aggaggcggt gtattcatac aatggaatac         9850
gattcagcaa taaaaaggca ttgagctact atgtgagcca taacacaggg         9900
caatgagaga agccagatgc taaagagcac ctacagtatg aatccattta         9950
taggagattc tagaacaggc aataactaat cgggagtggc agaaagcaga        10000
tcagtggttg cccggggcca gggctggata tggacactgt gaaatagcag        10050
gttggtaccc tccaggggga tggagatgtt ctaaattgag actggggttg        10100
tggttttatg ggtgtatcac tggctggact attttaaatg gatgcacttt        10150
gttatatgta aattatacct caataaagat gacttaaaga gttaaaaaaa        10200
aaaaaaaaaa aaagaaccac gagaatgaar acctgatcct tgtcttgctt        10250
acagtctagt gaaaacgmca gatgtgaaaa caaacaacca taaggcggtg        10300
agtagcctaa gaagcatgct caaataacaa gagttctgtt tatgaagggc        10350
tccctcgcgc cagacccaca gaggtggctt ggcgtcactg ttctagaagt        10400
ccagataaga aaagaggctg agatggaggg gaagttgttc acgcaggatt        10450
actcagctag aatcagcagg cctgggactg ggctccaagg ctgcctgggt        10500
tcagagcagg tgccacagca gcctgtggca ggacaccgag cagagagctc        10550
gggactgttg cagcttctca ggtgagactt tgcggaggag gtattgacac        10600
aggagttgga atttgctcag cagagtagag gatgcgggga aggaaatttc        10650
aaagcaaagg gaacaaacaa tatgagcaaa ggctgggcaa cacttgtgag        10700
aaggcagggt tcctgggaat ggagagacgt gtcccgaaaa gagcagaaga        10750
ggtcaacagg atattacatg ttcttcgcat tcacttattt ttttaagaac        10800
ctattaagca ataattttta cgagaggcaa cagctctgca gggcaggcaa        10850
```

-continued

```
gtgawgtatg tgctcttggc aaacgcaggg aagaacccac cgtgatgcca     10900
aggttgcctc tttagggaaa ggggttctcc ctgtgacatt tctcctcctc     10950
caggaggtta aggctgtgtt ccaggatccc aggtttctgc tgaacaccct     11000
ttgtggcact ctttcacggt cctgagaaat cccaggagga aaaaaaaaaa     11050
aacaaaaacc cgcctgtgct tttatgctgg gctttctggc tggaggaagt     11100
caagtcactg gagcgaagca aaatgtgtca cactgtcatg gtgcgttctt     11150
ctggaaactc agcacagcag tgaggtttgg aggctttgag gctggactgg     11200
ctgaggtcag atctcagcgc tctttcacac tgattacttt cccctttctg     11250
cactttggct tctttagaag attgcaaaag aggggtgatc ataagagggc     11300
agatgtgaga atgaagggac agtacgtgca atgtgctcag tcagactcat     11350
cgagtctgag acgttaattt agcctgtata gccttttgta tgacagtcag     11400
tcctccataa atcagttttt taaaaagaag gtgcttagag cagagcctgg     11450
cccagagcaa acatttaata gacagtagct tttgtgtttt caaaaaggtg     11500
acatgcacat gtcatccctt ttattttgct gtgacccgtt ctttcagaga     11550
attataatga agcgggattt gggacatgtt gatcatatca tttaggatga     11600
ttgtgactct taacagaaca cccaacttag ggtggctcaa acaggaagga     11650
gatttctaaa tctcacattc tggggcgcct gggtggcaca gttggttaaa     11700
cattcgactc ttggttttgg ctcaggtcat gatctcaggg ttgtgagatg     11750
gggccctgtg ttggagtctg cgctcagctc acaattctct ctctcctcca     11800
cttctgcccc tcctgccctc tctaaaataa acatttgagg gtttttttaa     11850
aaagatttta tttagttagt tgagagagag acagacagag acagagagac     11900
agagagtgag catgtgtgag cacaggtggg gaagggcaga gggagcagca     11950
gaatccctgc tgagcaggaa gcccaacaca gggcttgatc ccaggaccaa     12000
gatcaagacc cgagccaaag gcagatgctc atccaactga gccagccagg     12050
caaccctaaa ataaatgtct ttttttaaaa aatcatcctg tgtttcactg     12100
aaactaacat gccattgctt gtgagatgcc ccttgcattc agaaatatta     12150
aaatataaaa atgtgtgtct ttgarttgaa acaaaaggtc tgaaggtagg     12200
gggctctagg actggtaatt tggcagttca ccatgaggac tctttgtcct     12250
ttgtttccac tctgccatcg tcagacctta ggctctggct ttgaggcaag     12300
cctcatggat gcaagatggc tgccagggcc tcaagcatca agtcttcaga     12350
gcctcccaaa gccagaagag aggctgctgt ttttaaaaac aagaaaaact     12400
ttcccaaact ttgcttaatt gcatcacaaa ccccttttctg aattcctggc     12450
agaaggaata gatttatcat aagggtctgg tgccgactct tcaagattcg     12500
cccttagggc cggggaggag cttgcctcca ctgaagcacc gagctccagt     12550
tctgttgtga gatggaggaa gaacagctgt gagctggcaa tgagcagcgc     12600
tgccatacag atraaccgcc tgtgaatcac cggtcaactg tgcccgacag     12650
aagcagctga ctgcttggga tattcctacc caccttcctg ttcctatcaa     12700
caatggtaga gcttcctctc caggttaaga aattaacctc catattccaa     12750
agacttggtt tcctattaat gtggctttcg ggtaccgtat ccaaaatcct     12800
```

-continued

```
atccggatgg aacccagtga gttagccacc tgagcacagc aggccaatgg    12850
actagatttc acctccgtgc tcagagccaa ggccccctga ccgcaccgag    12900
gactgtggcc ttgctcagcc tgggatctac ttctgtcact gaccactaga    12950
ttgggggact ccgtgtcagt gaatacagat ccatgctagc ctaggatgac    13000
ggctacgtaa caattccact gcacataaaa actcaagtgt cccagacctc    13050
ggggcgcctg gctggcttag ggaggactga ctcttaatct cagagtcttg    13100
agttcaagcc ctgtgttggg tgtggagcct acttaaaaaa aaaaagaaga    13150
agaagaagaa ggagaaggag aaggagaagg agaaggagaa ggagaaggag    13200
aaggagaaga agaagaagaa gaagaagaag aagaagaaga agaagaagaa    13250
gaaagaagaa gaagaagaag aagaagaatt agaaatcaca acattgatgc    13300
tttgatctcc acagctctga actcccgcct gctccttcag aaatctgatg    13350
cgttctctgt tgtctttcca ctgatttttt tctttttttt ttaagatttt    13400
atttatttga cacacagaga gatcagcagg gggagcatca gagggagagg    13450
gagcagcagg ctccccgctg agcaggaagt ccaacatggg gctcaatccc    13500
aggaccctgg gatcatgacc tcagccaaag gcagatgttt aacccactga    13550
gccacccagg tggccctgat ttttttttta agattattta tttattttag    13600
ggatccctgg gtggcgcagc ggtttaccgc ctgcctttgg cccagggcgc    13650
aatcctggag acctgggatc gagtgccaca tcgggctccc ggtgcatggg    13700
gcctgcttct ccctctgcct atgtttctgc ctctctctct ctctctgtgt    13750
gactacaata aattaaaaaa tattttttaa tattatttat ttattttaaa    13800
atattttatt tatttattca tgagagacac agagagagag gcagagatac    13850
aggcagaggg agaagtaggc tcccacagga cttgatccca ggaccccagg    13900
atcacgacct gaatccaagg cagatgctca accactgagc cacccaggtg    13950
tcccattaaa gattatttat ttgacagaga gagagagagc aggagcagag    14000
gggcacaggg agaagaagac ttcctgctga tcgaggagcc cgacatgggg    14050
cttgaaccta gaaccctaag atcatgaccc aagttgaagg cagatgctta    14100
accaatggag ccaccaggtg ccccatcctc ccctatttct ggactgccca    14150
ggcagtgtgc cctctgcctg ccactcttcc tgcttgtgtg ctctattttt    14200
caaataaata aattaattaa aaaataataa tcttgaggca cctgggtggc    14250
tcagtggttg aacatctgtc tttggctcag ggcgtgatcc tggggtcctg    14300
ggatcgagtc ccacattggg ctccctggat ggagactgct tctctctctg    14350
cctgtgtctc tgcctctctc tctctgtgtg tgtgtgtctc tcatgaataa    14400
ataaataaaa gggatccctg ggtggcacag tggtttagcg cctgcctttg    14450
gcccagggcg cgatcctgga gacctgggat cgaatcccac gtcgggctcc    14500
cggtgcatgg agcctgcttc tccctctgcc tatgtctggg atccctgggt    14550
ggcacagcgg tttggtgcct gcctttgggc cagggcgtga tcctggagac    14600
ccgggatcga atcccacatc gggctcccgg tgcatggagc ctgcttctcc    14650
ttctgcctgt gtctctgcct ctctctctct ctgtgtgact atcatgaata    14700
aataaataaa atcttaaaaa aaaaataaat aaataaaatc tttttattag    14750
attttattta aatcttttta ttagatttta atctcactgc gttttgctcc    14800
```

-continued

```
ggcctctcgg cgcctgccca gccacccgag acatgccacc tgcggtgaac     14850
ctgctgctct tctactaggt gtcctgtcag gtgtgaaagc tccactgtag     14900
accgtggcat tgtggctcct ctcaagccca gaagaatgct ccatgctcct     14950
cacacgcact agctggcaac cggtctggga ctcaagacag ccctgctaga     15000
gcccagagcc ccccagtctt gcagccatca gcycctgcag cctctcctcc     15050
tcactctgct tgccataaag tggctcaaaa ccacggaaca ggtgcccatc     15100
attcccctga gtaatttcat cccaaccacc cctgcaaaca cacaaaaccc     15150
ttctttgctc ctctccccca tgcccaaaag ccctatagta agactgatgt     15200
atagatatac gaagttcagt acatcttagt ggtgagagta tggactctgc     15250
aggctggcct caaaccttga ccccagcaat cactagttgt gtgaatttgg     15300
gaaagtcacc tcatctctca ctcacctcac ctcatctgcg aaatgcrggt     15350
agtgatagwg cccttcagag ggcagcggtg cacattaaac aaattggtgt     15400
gcgttcagta ctccaggagt ggacggcgca tggtaagtgc taccyggtat     15450
ccactctcgc tgttattcgg cctgcagcgg gtcccttgcc tccatccaag     15500
cagctctggg gaacttccac attcaaaact ccctctccga gtctgaaaat     15550
gaaaggaact tagttttcag ggagagagcc cattcctcct ttccctattc     15600
tacaaaactg tattcaaggg caagacagaa atgcaagggc cagtttcata     15650
agacagatgt tactgccaag tgagtcaatg attatctgtt gtgtacgtgg     15700
gcagaggcag aggaataaca accagactct gggaggcaat taaaaagaaa     15750
aaaaaaaaaa gtaaaagagt gtctcatgga gcgcctgggt ggctcagtcc     15800
gttaagcctt ggacttttgg tttcccctca ggtcatgatc tcagggtcgt     15850
gggacccagc cctggggcgg gctctgtgat cagtggggag cctgcttgag     15900
attccctcct tctgctgtgc acactctctc tctaaaataa atacgtcttt     15950
agaagagcaa gcgagcgaga gatgcttccc gcctagaaga gcttacaatc     16000
aaatcaaggg aggcaaacat aaacaagtgt ggcaacttga taataagcac     16050
ctgcgaccta tggccataca cagaataaca taacccagac taaatgccac     16100
tgcatagtca ctagcgggtt gatgacaacg gggggaggct aatgctgaaa     16150
aggcctttct gtcttataag tttaaactaa tttctggggg cacctgggtg     16200
gctctggttg agcatctgcc tttgggtcgt cgtcccaggg tcctgagatc     16250
gagtccctca tccggctccc agccccgtag gagcctgctt ctccctctgc     16300
ctcttcctct ctgtctctca tgaataaata aataaaaatt ttaagggatg     16350
cccgggtggc tcagcggttt agcgcctgcc tttggcccag ggtgtgatcc     16400
tggggtcccg agatcgagtc ccacatcgag tcccacatcg agttccggga     16450
tcgagtccct gcagggaacc tgcttctccc tctccctgtg tgtgtgtctc     16500
tctctctttc tgtatctctc atgaataaat aaagaaaatc tttaaaaata     16550
aataaataaa aacagtattt aaaaaaatga actaatttcc aagtaggtgt     16600
aaattctggc tcggactagt gaatggctct ggctctgctg catcacccac     16650
cgccagggct ctgggccgct ccgagccccg ctcgccggcg ccccctgccg     16700
cccgggcctc ccgccttcac cccaacccgc agggcggcgg agccctaggc     16750
```

-continued

```
ccaatcggcc ccgggaacct gccgcctctt ctctagcgca acccagcacc         16800

cagatgaccc cttttccgcc ccaggtgcag tccggccggg ccctggtgtc         16850

ctcacccgtt cccctaggga gacccctctc gaaccttctg cgccacccta         16900

ctctacgcca gggaaaatct gtgcactcag tagataaatg cttgtaactg         16950

aagcaaccgt ctccgtggct ccagaatcgc gctgaggatg ctgctgccgc         17000

acccccacct cccccggctc cggcggaggt tgtttggact acacttccca         17050

tgaggcccct ctcaacatcg cgataactct cgcgagaccg ctgggaagag         17100

ttgtgcgcag gcgcagcccc gccttcttgt cgaggcaggc cgcgtggccg         17150

gcagtcatgg cggctccttg ctggcccgac cgggacaggg agtctggagy         17200

ctctggctgt ggtaaggttg tcgaggcggg cagacgggat cgtccttggc         17250

ccggcgctag ttcgctcggc ctccctttcc tcgggggcgg gatgatgacg         17300

gtaaagccgg tcttcctcgt agggtggttg ggttagttga gatgctggat         17350

cggaaaaacgc tttctgagcg gcgcgagtgt tgacgatcga agggagagag        17400

ctcaggcccc ccttggagtc agagggcccc tcctgggggg gggggtcctc         17450

cagcctgtgc agccccgtgt gtgccctgcg ggtctcccgg gcccgcccac         17500

gggaggctgc cggtggtagt tcttaatcca catcaagtgt taacgtgagg         17550

gtcctggagt gccccgaggt cggccctggt cagtggttcg tattcagtcc         17600

tacagatagt agtaaagggg cttgtagatt ttggaaagcc ataatgctct         17650

gcgccctacc ttccatgttc atttttttc ccctctctct tcccgtacag          17700

ggttttcttt gcgtcgcaga cctgcaggtt gaagcttaaa agtagcgaat         17750

ggggagccct gtgaaatggg taaggatggg tgctggcagg gcccgggtgg         17800

tgaccagaag tgagaaagtc gagatggtgg gcaggcctgc cacacccggc         17850

cgccgcacgc tttactttac taattttatt ttttttaaa grtttaatta          17900

attaattaat taatgatagg cagagacaca ggcagaggga gaagcaggct         17950

ccgtgccggg agcccgacgc gggactccag gatcgcgccc tgggccaaag         18000

gcaggcgcca aaccgctgag ccacccaggg atcccacttt accgatttta         18050

agttcggttc ttaggaacac gtggacgcac gcatccggtt agggtgagaa         18100

gaaaacggac ccgggtcctg gaagcgagca gggccttgcc agtgtgactc         18150

ggcgccgcta ggtgtcactg tttggattca aaccggttgc cgcgcacgag         18200

gttggcgggg aggcttagga aatgggcttc ggtggggttt ggaagtattt         18250

gtggatgatt taaagttatc tttgtcttaa agggctcttt tgtgaagagt         18300

tttgatgcgt tgaggctcag cttttttttt tttttttttt taaggtttgt         18350

attcattttt tcacagagag gcagagggag gagaagcttg ctgcctgcag         18400

agagcaggat gcgagactcg atccctggat ttcgggatca cgcccagagc         18450

caaaggcaga cacgcaacta ctgagccacc caggcgtccc gaggccccag         18500

cttcttaaat aaccaatctt gagaataaca tcttgacctc atttctctta         18550

gaatatactt tgttacattt cccttagaga ttaaaggtgt tg                 18592
```

<210> SEQ ID NO 2
<211> LENGTH: 54
<212> TYPE: PRT
<213> ORGANISM: canis familiaris -continued

<400> SEQUENCE: 2

```
Met Cys Thr Thr Leu Phe Leu Leu Ser Thr Leu Ala
                 5                  10

Met Leu Trp Arg Arg Arg Phe Ala Asn Arg Val Gln
        15                  20

Pro Glu Pro Ser Gly Ala Asp Gly Ala Val Val Gly
 25                  30                  35

Ser Arg Ser Glu Arg Asp Leu Gln Ser Ser Gly Arg
             40                  45

Lys Glu Glu Pro Leu Lys
     50
```

<210> SEQ ID NO 3
<211> LENGTH: 695
<212> TYPE: DNA
<213> ORGANISM: canis familiaris

<400> SEQUENCE: 3

```
agtggcagca ggaacctcag gatgggcagc agtggcttgt gagagccggc       50

agggccattt tggcctttct cctgcagact ctgtccggga ggggatgggg      100

cagctgagcc atgtrcacca ccctcttcct actcagcacc ttggccatgc      150

tctggcgccg ccggttcgcc aaccgggtcc aaccggagcc cagcggagca      200

gacggggcag tcgtgggcag caggtcggag agagacctcc agtcctcggg      250

cagaaaggaa gagcctctga agtaagtctt cacccggtca ggcggagctc      300

ggccccaggg aytgggatca gctggcagag gcagttcaag tcccggctgg      350

cctcttaccc acaaagcatg ctgtggtgga agcagcagca gcagcaagaa      400

gaaaaatggg aaaaagcagt catcaagaag gtagactcct ccctttgagt      450

ccctggacct gcctggcctc cctttgcccc agaccctggt ggtggggctc      500

ctgaagcaag gcctggctgg ggcaggctgg agggcaaaga cgctcattgc      550

cctggcttgg gctcccttcc tctgagatcc tgaggatagt ctgaggcagg      600

cccagagagg gactcaggtt tcttatggaa ggrcttctca ttcatcccta      650

atataatcct tgcaatgacc caaaaaaaaa aaaaaaaaaa aaaaa           695
```

<210> SEQ ID NO 4
<211> LENGTH: 20
<212> TYPE: DNA
<213> ORGANISM: artificial sequence
<220> FEATURE:
<223> OTHER INFORMATION: RT-PCR forward primer

<400> SEQUENCE: 4

```
caccttggcc atgctctggc                                        20
```

<210> SEQ ID NO 5
<211> LENGTH: 25
<212> TYPE: DNA
<213> ORGANISM: artificial sequence
<220> FEATURE:
<223> OTHER INFORMATION: RT-PCR reverse primer

<400> SEQUENCE: 5

```
aatgcatata aataaagcac ttggc                                  25
```

-continued

```
<210> SEQ ID NO 6
<211> LENGTH: 18
<212> TYPE: DNA
<213> ORGANISM: artificial sequence
<220> FEATURE:
<223> OTHER INFORMATION: RT-PCR forward primer

<400> SEQUENCE: 6

ccagtggcag caggaacc                                                    18


<210> SEQ ID NO 7
<211> LENGTH: 18
<212> TYPE: DNA
<213> ORGANISM: artificial sequence
<220> FEATURE:
<223> OTHER INFORMATION: RT-PCR reverse primer

<400> SEQUENCE: 7

ccaagccagg gcatgagc                                                    18


<210> SEQ ID NO 8
<211> LENGTH: 29
<212> TYPE: DNA
<213> ORGANISM: artificial sequence
<220> FEATURE:
<223> OTHER INFORMATION: reverse primer located on exon 1

<400> SEQUENCE: 8

ccaaggtgct gagtaggaag agggtggtg                                        29


<210> SEQ ID NO 9
<211> LENGTH: 27
<212> TYPE: DNA
<213> ORGANISM: artificial sequence
<220> FEATURE:
<223> OTHER INFORMATION: reverse primer located on exon 3

<400> SEQUENCE: 9

agtccctggg gccgagctcc gcctgac                                          27


<210> SEQ ID NO 10
<211> LENGTH: 29
<212> TYPE: DNA
<213> ORGANISM: artificial sequence
<220> FEATURE:
<223> OTHER INFORMATION: forward primer located on exon 1

<400> SEQUENCE: 10

caccaccctc ttcctactca gcaccttgg                                        29


<210> SEQ ID NO 11
<211> LENGTH: 28
<212> TYPE: DNA
<213> ORGANISM: artificial sequence
<220> FEATURE:
<223> OTHER INFORMATION: forward primer located on exon 3

<400> SEQUENCE: 11

agggactggg atcagctggc agaggcag                                         28


<210> SEQ ID NO 12
<211> LENGTH: 1084
<212> TYPE: DNA
<213> ORGANISM: artificial sequence
<220> FEATURE:
<223> OTHER INFORMATION: EST clone contig
```

<400> SEQUENCE: 12

```
gagcagctgc agcagctgcc actgccctgt gtcaccccag ggtgcaaatg          50

ccaccacggg gagcaccccg cccatcccga actgtgtggc tgtgcagatg         100

cgggcaggat ggtcctgggc acaggccttg gtccaagacc aggcaggcgt         150

ggtacttgat ctgaggtggg catcatggca caggagctgg tcccaggggt         200

gcccggggac ctttatagaa cctcagtcgg gaagaagccc aagaccttga         250

gccagaggga agtaatgctt ctttgtgagc ctcaaaagga gggaaatggc         300

caaggtttac agtaatataa tgacactaat attattatta ataatggcta         350

atgtgtctca aacgcttctt acgtgctagg cgctgtgcca agtgctttat         400

ttatatgcat tgtctcattt atggggcagg aactgttgtc agtctcattt         450

acccaataag gaaagtgctt gctcaaggtc acccacagtg agtagtgaag         500

ccaggacgtg ttccccggca aggtgatgta aaagcctgtg aaggtattgg         550

gcctcgagga catcctggga gtgtgacctg tccaccaggg cacagggcat         600

gagagctggc aaccctccct ggtgatactg ccgctgctca gtctgcagaa         650

actcatcatt ccaggctgga ccagactctg ggccccgagg gcagtgacca         700

gagccacctt tccaggatct gtcatgctcc tcagggagga agcagtggcc         750

actggcaggg atgacagata tcaaggttgt cactcattgc tgctgttgct         800

ctgctgtttc ctccaaccag gggcagagcc ctgggggtaa gggagggtgg         850

cagccagcag cccagccaga gaaggaggag ccagaggagg aaggctttgt         900

tgtttgtttt tacaggggga cggtgcaggg ctttaaggag gtggcttcaa         950

gacctgctga ctttagccat aaactggtac ctaagggtgc tggaccctct        1000

ctgtgggata catatgcccc ctagtgggga ttaagcctgg agggtggctg        1050

agaaattaaa gcaaaaaaaa aaaaaaaaaa aaaa                         1084
```

<210> SEQ ID NO 13
<211> LENGTH: 707
<212> TYPE: DNA
<213> ORGANISM: artificial sequence
<220> FEATURE:
<221> NAME/KEY: unsure
<222> LOCATION: 598, 602
<223> OTHER INFORMATION: Clone 9 sequence; RT-PCR product; n is g, a, t or c

<400> SEQUENCE: 13

```
caccttggcc atgctctggc gccgccggtt cgccaaccgg gtccaaccgg          50

agcccagcgg agcagacggg gcagtcgtgg gcagcaggtc ggagagagac         100

ctccagtcct cgggcagaaa ggaagagcct ctgaagtaag tcttcacccg         150

gtcaggcgga gctcggcccc agggactggg atcagctggc agaggcagtt         200

caagtcccgg ctggcctctt acccacaaag catgctgtgg tggaagcagc         250

agcagcagca agaagaaaaa tgggaaaaag cagtcatcaa gaaggtagac         300

tcctcccttt gagtccctgg acctgcctgg cctccctttg ccccagaccc         350

tggtggtggg gctcctgaag caaggcctgg ctggggcagg ctggagggca         400

aagacgctca ttgccctggc ttgggctccc ttcctctgag atcctgagga         450

tagtctgagg caggcccaga gagggactca ggtttcttat ggaaggrctt         500
```

-continued

```
ctcattcatc cctaatataa tccttgcaat gaccccaaga ccttgagcca       550

gagggaagta atgcttcttt gtgagcctca aaaggaggga aatggccnag       600

gnttacagta atataatgac actaatatta ttattaataa tggctaatgt       650

gtctcaaacg cttcttacgt gctaggcgct gtgccaagtg ctttatttat       700

atgcatt                                                      707
```

<210> SEQ ID NO 14
<211> LENGTH: 562
<212> TYPE: DNA
<213> ORGANISM: artificial sequence
<220> FEATURE:
<223> OTHER INFORMATION: RT-PCR exons 1-4

<400> SEQUENCE: 14

```
ccagtggcag caggaacctc aggatgggca gcagtggctt gtgagagccg        50

gcagggccat tttggccttt ctcctgcaga ctctgtccgg gaggggatgg       100

ggcagctgag ccatgtrcac caccctcttc ctactcagca ccttggccat       150

gctctggcgc cgccggttcg ccaaccgggt ccaaccggag cccagcggag       200

cagacggggc agtcgtgggc agcaggtcgg agagagacct ccagtcctcg       250

ggcagaaagg aagagcctct gaagtaagtc ttcacccggt caggcggagc       300

tcggccccag ggactgggat cagctggcag aggcagttca agtcccggct       350

ggcctcttac ccacaaagca tgctgtggtg gaagcagcag cagcagcaag       400

aagaaaaatg ggaaaaagca gtcatcaaga aggtagactc ctccctttga       450

gtccctggac ctgcctggcc tccctttgcc ccagaccctg gtggtggggc       500

tcctgaagca aggcctggct ggggcaggct ggagggcaaa gacgctcatt       550

gccctggctt gg                                                562
```

<210> SEQ ID NO 15
<211> LENGTH: 21
<212> TYPE: DNA
<213> ORGANISM: artificial sequence
<220> FEATURE:
<223> OTHER INFORMATION: RT-PCR forward primer from exon 3

<400> SEQUENCE: 15

```
cagtcgtggg cagcaggtcg g                                       21
```

<210> SEQ ID NO 16
<211> LENGTH: 25
<212> TYPE: DNA
<213> ORGANISM: artificial sequence
<220> FEATURE:
<223> OTHER INFORMATION: RT-PCR reverse primer from exon 8

<400> SEQUENCE: 16

```
aatgcatata aataaagcac ttggc                                   25
```

<210> SEQ ID NO 17
<211> LENGTH: 316
<212> TYPE: DNA
<213> ORGANISM: artificial sequence
<220> FEATURE:
<223> OTHER INFORMATION: RT-PCR product

<400> SEQUENCE: 17

```
cagtcgtggg cagcaggtcg gagagagacc tccagtcctc gggcagaaag        50
```

-continued

```
gaagagcctc tgaagtaagt cttcacccgg tcaggcggag ctcggcccca        100

ggggtgcccg gggaccttta tagaacctca gtcgggaaga agcccaagac        150

cttgagccag agggaagtaa tgcttctttg tgagcctcaa aaggagggaa        200

atggccaagg tttacagtaa tataatgaca ctaatattat tattaataat        250

ggctaatgtg tctcaaacgc ttcttacgtg ctaggcgctg tgccaagtgc        300

tttatttata tgcatt                                             316


<210> SEQ ID NO 18
<211> LENGTH: 20
<212> TYPE: DNA
<213> ORGANISM: artificial sequence
<220> FEATURE:
<223> OTHER INFORMATION: RT-PCR forward primer from exon 2

<400> SEQUENCE: 18

gcagcaggtc ggagagagac                                          20


<210> SEQ ID NO 19
<211> LENGTH: 22
<212> TYPE: DNA
<213> ORGANISM: artificial sequence
<220> FEATURE:
<223> OTHER INFORMATION: RT-PCR reverse primer from exon 5

<400> SEQUENCE: 19

cttccctcag atgtggagtc ag                                       22


<210> SEQ ID NO 20
<211> LENGTH: 796
<212> TYPE: DNA
<213> ORGANISM: artificial sequence
<220> FEATURE:
<223> OTHER INFORMATION: RT-PCR product no. 1

<400> SEQUENCE: 20

gccaccgggt ccaccggagc ccagcggagc agacggggca gtcgtgggca         50

gcaggtcgga gagagacctc cagtcctcgg gcagaaagga agagcctctg        100

aagtaagtct tcacccggtc aggcggagct cggccccagg gactgggatc        150

agctggcaga ggcagttcaa gtcccggctg gcctcttacc cacaaagcat        200

gctgtggtgg aagcagcagc agcagcaaga agaaaaatgg gaaaaagcag        250

tcatcaagaa gtttccaggg cacttgcctc tccccggtcc ccagagctca        300

ccccgtcacc agccactctg ctgcagttct caataagaaa tgccagctgg        350

gatctgtgac atgtctgcct gcggctggaa ggaagcatct ctcaacctgt        400

cctctgagcg tgtctgcgtg cctgtgtgca tgcgtgcgtg tgttccaaag        450

gggcagtcgc atgtgggaag ggaagaagcc tgacacttgt tcttgtcaat        500

ctgctgactg ctcagtacca cggcggctct gccatttctc cctcacagtc        550

ctgctcgacc cagagcagag atcaaagcag atttccgctt ctgctccctg        600

agatccaggc gcagacctgc aggcagctgc tccccactgt ctggaagcca        650

ttcatcatgc aaagcgcctc cccaccaaac ccctgcctgc acgtgcatcg        700

tccccccacc atcaccatcc agcccccagg gtgggcaggg aggtccctgc        750

ctagctgcac accccccagg ccatcaagag gcaggagatg ggagt             796
```

<210> SEQ ID NO 21
<211> LENGTH: 763
<212> TYPE: DNA
<213> ORGANISM: artificial sequence
<220> FEATURE:
<223> OTHER INFORMATION: RT-PCR product no. 2

<400> SEQUENCE: 21

```
gccaccgggt ccaccggagc ccagcggagc agacggggca gtcgtgggca     50

gcaggtcgga gagagacctc cagtcctcgg gcagaaagga agagcctctg    100

aagtaagtct tcacccggtc aggcggagct cggccccagg gactgggatc    150

agctggcaga ggcagttcaa gtcccggctg gcctcttacc cacaaagcat    200

gctgtggtgg aagcagcagc agcagcaaga agaaaaatgg gaaaaagcag    250

tcatcaagaa gagctcaccc cgtcaccagc cactctgctg cagttctcaa    300

taagaaatgc cagctgggat ctgtgacatg tctgcctgcg gctggaagga    350

agcatctctc aacctgtcct ctgagcgtgt ctgcgtgcct gtgtgcatgc    400

gtgcgtgtgt tccaaagggg cagtcgcatg tgggaaggga agaagcctga    450

cacttgttct tgtcaatctg ctgactgctc agtaccacgg cggctctgcc    500

atttctccct cacagtcctg ctcgacccag agcagagatc aaagcagatt    550

tccgcttctg ctccctgaga tccaggcgca gacctgcagg cagctgctcc    600

ccactgtctg gaagccattc atcatgcaaa gcgcctcccc accaaacccc    650

tgcctgcacg tgcatcgtcc ccccaccatc accatccagc cccagggtg     700

ggcagggagg tccctgccta gctgcacacc ccccaggcca tcaagaggca    750

ggagatgggg agt                                            763
```

<210> SEQ ID NO 22
<211> LENGTH: 509
<212> TYPE: DNA
<213> ORGANISM: artificial sequence
<220> FEATURE:
<223> OTHER INFORMATION: RT-PCR product no. 3

<400> SEQUENCE: 22

```
gccaccgggt ccaccggagc ccagcggagc agacggggca gtcgtgggca     50

gcaggtcgga gagagacctc cagtcctcgg gcagaaagga agagcctctg    100

aagtaagtct tcacccggtc aggcggagct cggccccagg gactgggatc    150

agctggcaga ggcagttcaa gtcccggctg gcctcttacc cacaaagcat    200

gctgtggtgg aagcagcagc agcagcaaga agaaaaatgg gaaaaagcag    250

tcatcaagaa gtcctgctcg acccagagca gagatcaaag cagatttccg    300

cttctgctcc ctgagatcca ggcgcagacc tgcaggcagc tgctccccac    350

tgtctggaag ccattcatca tgcaaagcgc ctccccacca aacccctgcc    400

tgcacgtgca tcgtcccccc accatcacca tccagccccc agggtggca     450

gggaggtccc tgcctagctg cacacccccc aggccatcaa gaggcaggag    500

atggggagt                                                 509
```

<210> SEQ ID NO 23
<211> LENGTH: 17
<212> TYPE: DNA
<213> ORGANISM: artificial sequence -continued

```
<220> FEATURE:
<223> OTHER INFORMATION: Pyrosequencing forward primer

<400> SEQUENCE: 23

ttgtgagagc cggcagg                                                    17


<210> SEQ ID NO 24
<211> LENGTH: 20
<212> TYPE: DNA
<213> ORGANISM: artificial sequence
<220> FEATURE:
<223> OTHER INFORMATION: Pyrosequencing biotin labeled reverse primer

<400> SEQUENCE: 24

atggccaagg tgctgagtag                                                 20


<210> SEQ ID NO 25
<211> LENGTH: 15
<212> TYPE: DNA
<213> ORGANISM: artificial sequence
<220> FEATURE:
<223> OTHER INFORMATION: Pyrosequencing oligo probe

<400> SEQUENCE: 25

ggggcagctg agcca                                                      15


<210> SEQ ID NO 26
<211> LENGTH: 113
<212> TYPE: DNA
<213> ORGANISM: artificial sequence
<220> FEATURE:
<223> OTHER INFORMATION: Pyrosequencing PCR product

<400> SEQUENCE: 26

ttgtgagagc cggcaggggc cattttggcc tttctcctgc agactctgtc                50

cgggaggga tggggcagct gagccatgtr caccaccctc ttcctactca                100

gcaccttggc cat                                                       113


<210> SEQ ID NO 27
<211> LENGTH: 18
<212> TYPE: DNA
<213> ORGANISM: artificial sequence
<220> FEATURE:
<223> OTHER INFORMATION: forward primer

<400> SEQUENCE: 27

ccagtggcag caggaacc                                                   18


<210> SEQ ID NO 28
<211> LENGTH: 21
<212> TYPE: DNA
<213> ORGANISM: artificial sequence
<220> FEATURE:
<223> OTHER INFORMATION: reverse primer

<400> SEQUENCE: 28

ccgacctgct gcccacgact g                                               21


<210> SEQ ID NO 29
<211> LENGTH: 21
<212> TYPE: DNA
<213> ORGANISM: artificial sequence
<220> FEATURE:
<223> OTHER INFORMATION: RT-PCR forward primer
```

<400> SEQUENCE: 29
agtggcagca ggaacctcag g 21

<210> SEQ ID NO 30
<211> LENGTH: 26
<212> TYPE: DNA
<213> ORGANISM: artificial sequence
<220> FEATURE:
<223> OTHER INFORMATION: RT-PCR reverse primer

<400> SEQUENCE: 30
ggattatatt agggatgaat gagaag 26

<210> SEQ ID NO 31
<211> LENGTH: 22
<212> TYPE: DNA
<213> ORGANISM: artificial sequence
<220> FEATURE:
<223> OTHER INFORMATION: RT-PCR forward primer

<400> SEQUENCE: 31
ttaatcagtc tgcacaaggt cg 22

<210> SEQ ID NO 32
<211> LENGTH: 25
<212> TYPE: DNA
<213> ORGANISM: RT-PCR reverse primer
<220> FEATURE:
<223> OTHER INFORMATION: amplification primer

<400> SEQUENCE: 32
gggtcattgc aaggattata ttagg 25

<210> SEQ ID NO 33
<211> LENGTH: 1015
<212> TYPE: DNA
<213> ORGANISM: artificial sequence
<220> FEATURE:
<223> OTHER INFORMATION: RT-PCR splice variant product no. 1

<400> SEQUENCE: 33
ttaatcagtc tgcacaaggt cgggttggct gaccccacta atcagcttga 50
gcctcctaat ccagtggcag caggaacctc aggatgggca gcagtggctt 100
gtgagagccg gcagggccat tttggccttt ctcctgcaga ctctgtccgg 150
gaggggatgg ggcagctgag ccatgtrcac caccctcttc ctactcagca 200
ccttggccat gctctggcgc cgccggttcg ccaaccgggt ccaaccgtga 250
gaagctgatg gggccatggg cagggatggg gagagaggag aagctagggg 300
gtgaggggtg gtgcaggggc tgcctggacc tcctgggagg ctggagggcg 350
gggaggattt gcagggaggt ccagagaggt ttcccatcag agcacgcggg 400
ggcgggggct cgcaggtgct ccgagactgg ctggagtccc cggtccccca 450
gcccaacacg gccaggagag ggggttctgg gcccgggcgc tgcccacagc 500
tcttccagcc tcttcctccc gcccacaggg agcccagcgg agcagacggg 550
gcagtcgtgg gcagcaggtc ggagagagac ctccagtcct cgggcagaaa 600
ggaagagcct ctgaagtaag tcttcacccg gtcaggcgga gctcggcccc 650
agggactggg atcagctggc agaggcagtt caagtcccgg ctggcctctt 700
acccacaaag catgctgtgg tggaagcagc agcagcagca agaagaaaaa 750

-continued

```
tgggaaaaag cagtcatcaa gaaggtagac tcctcccttt gagtccctgg          800

acctgcctgg cctccctttg ccccagaccc tggtggtggg gctcctgaag          850

caaggcctgg ctggggcagg ctggagggca aagacgctca ttgccctggc          900

ttgggctccc ttcctctgag atcctgagga tagtctgagg caggcccaga          950

gagggactca ggtttcttat ggaagggctt ctcattcatc cctaatataa         1000

tccttgcaat gaccc                                               1015


<210> SEQ ID NO 34
<211> LENGTH: 733
<212> TYPE: DNA
<213> ORGANISM: artificial sequence
<220> FEATURE:
<223> OTHER INFORMATION: RT-PCR splice variant product no. 2

<400> SEQUENCE: 34

ttaatcagtc tgcacaaggt cgggttggct gaccccacta atcagcttga           50

gcctcctaat ccagtggcag caggaacctc aggatgggca gcagtggctt          100

gtgagagccg gcagggccat tttggccttt ctcctgcaga ctctgtccgg          150

gaggggatgg ggcagctgag ccatgtrcac caccctcttc ctactcagca          200

ccttggccat gctctggcgc cgccggttcg ccaaccgggt ccaaccggag          250

cccagcggag cagacggggc agtcgtgggc agcaggtcgg agagagacct          300

ccagtcctcg ggcagaaagg aagagcctct gaagtaagtc ttcacccggt          350

caggcggagc tcggccccag ggactgggat cagctggcag aggcagttca          400

agtcccggct ggcctcttac ccacaaagca tgctgtggtg gaagcagcag          450

cagcagcaag aagaaaaatg ggaaaaagca gtcatcaaga aggtagactc          500

ctccctttga gtccctggac ctgcctggcc tccctttgcc ccagaccctg          550

gtggtggggc tcctgaagca aggcctggct ggggcaggct ggagggcaaa          600

gacgctcatt gccctggctt gggctccctt cctctgagat cctgaggata          650

gtctgaggca ggcccagaga gggactcagg tttcttatgg aagggcttct          700

cattcatccc taatataatc cttgcaatga ccc                            733
```